(12) United States Patent
Matsuda et al.

(10) Patent No.: US 10,690,629 B2
(45) Date of Patent: Jun. 23, 2020

(54) GAS DETECTION DEVICE

(71) Applicant: Toyota Jidosha Kabushiki Kaisha, Toyota-shi, Aichi-ken (JP)

(72) Inventors: Kazuhisa Matsuda, Susono (JP); Kazuhiro Wakao, Susono (JP); Keiichiro Aoki, Shizuoka-ken (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 266 days.

(21) Appl. No.: 15/841,941

(22) Filed: Dec. 14, 2017

(65) Prior Publication Data

US 2018/0172633 A1 Jun. 21, 2018

(30) Foreign Application Priority Data

Dec. 19, 2016 (JP) .................. 2016-245413

(51) Int. Cl.
*G01N 27/49* (2006.01)
*G01N 27/30* (2006.01)
(Continued)

(52) U.S. Cl.
CPC ............ *G01N 27/49* (2013.01); *F01N 3/20* (2013.01); *F02D 41/1444* (2013.01);
(Continued)

(58) Field of Classification Search
CPC .......... F01N 2560/027; G01N 27/4175; G01N 27/4065; F02D 41/1438–1498; F02D 41/22–222
See application file for complete search history.

(56) References Cited

U.S. PATENT DOCUMENTS 6,083,370 A 7/2000 Kato et al.
2002/0043460 A1 4/2002 Ikeda
(Continued)

FOREIGN PATENT DOCUMENTS

CN 105393115 A 3/2016
JP H10232220 A 9/1998
(Continued)

OTHER PUBLICATIONS

U.S. Appl. No. 15/796,219, filed Oct. 27, 2017; Inventors: Keiichiro Aoki et al.

*Primary Examiner* — Gurpreet Kaur
*Assistant Examiner* — Steven E Rosenwald
(74) *Attorney, Agent, or Firm* — Dinsmore & Shohl LLP

(57) ABSTRACT

A gas detection device includes: an element portion; a voltage applying unit configured to apply a voltage across a first electrode and a second electrode on surfaces of a solid electrolyte; a current detecting unit configured to detect an output current flowing between the first electrode and the second electrode; and a measurement control unit. The measurement control unit acquires a parameter which has a correlation with a degree of change of the output current increasing as a concentration of sulfur oxides in an exhaust gas increases based on the output current, and performs determination of whether the concentration of sulfur oxides in the exhaust gas is equal to or higher than a predetermined value or detection of the concentration of sulfur oxides in the exhaust gas based on the acquired parameter.

7 Claims, 18 Drawing Sheets

(51) Int. Cl.
  *F01N 3/20* (2006.01)
  *G01N 33/00* (2006.01)
  *G01N 27/407* (2006.01)
  *G01N 27/419* (2006.01)
  *F02D 41/14* (2006.01)

(52) U.S. Cl.
  CPC ......... *F02D 41/1456* (2013.01); *G01N 27/30* (2013.01); *G01N 27/4074* (2013.01); *G01N 27/419* (2013.01); *G01N 33/0042* (2013.01); *F01N 2560/027* (2013.01); *F01N 2900/1402* (2013.01); *G01N 33/006* (2013.01)

(56) References Cited

U.S. PATENT DOCUMENTS

| | | | |
|---|---|---|---|
| 2003/0164023 A1 | 9/2003 | Gruenwald et al. | |
| 2016/0146085 A1* | 5/2016 | Mizutani | F01N 11/00 60/274 |
| 2016/0349206 A1* | 12/2016 | Hashida | G01N 33/0042 |

FOREIGN PATENT DOCUMENTS

| | | | |
|---|---|---|---|
| JP | 2002071633 A | 3/2002 | |
| JP | 2009053108 A | 3/2009 | |
| JP | 2015017931 A | 1/2015 | |
| JP | 2015-155850 A | 8/2015 | |
| WO | 2015004846 A1 | 1/2015 | |
| WO | 2015/124985 A1 | 8/2015 | |

* cited by examiner

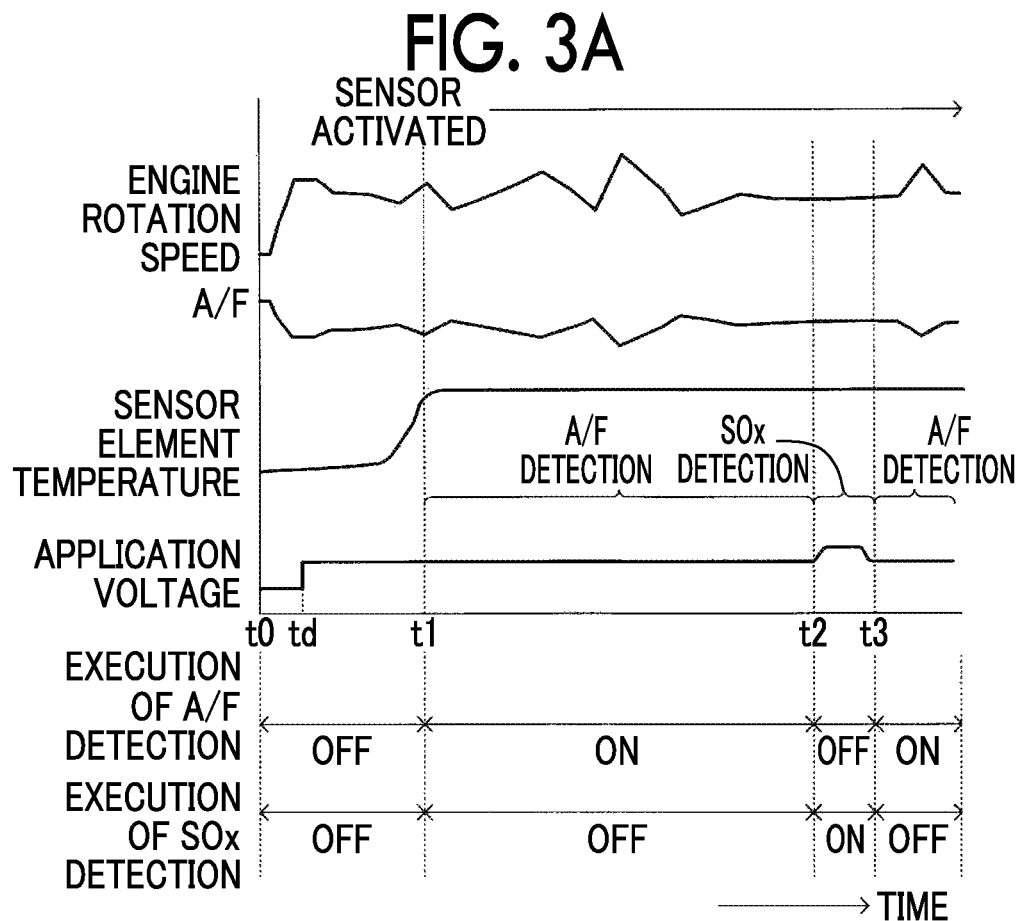
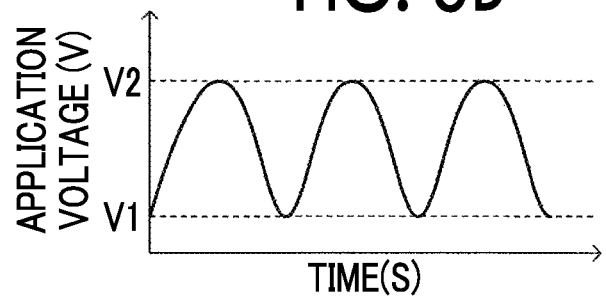
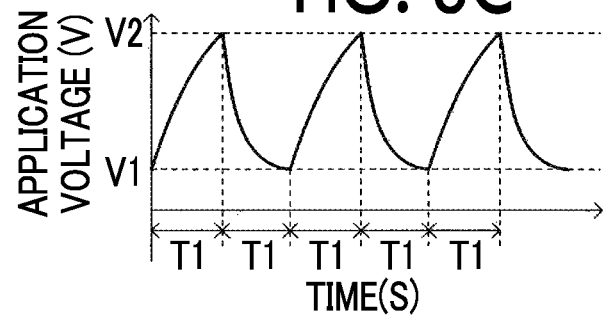

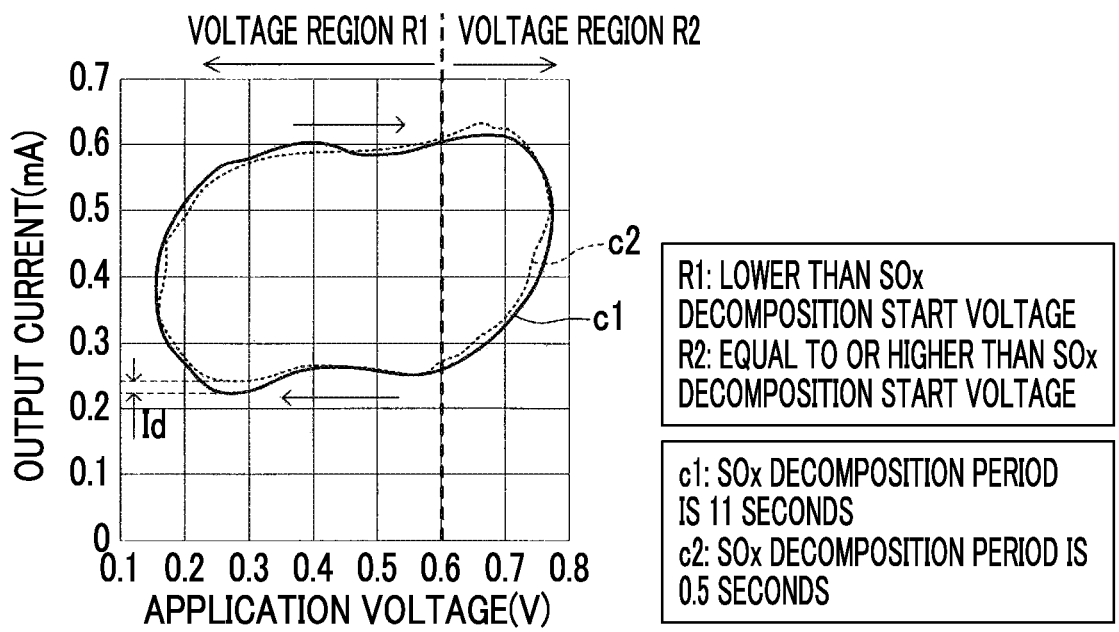
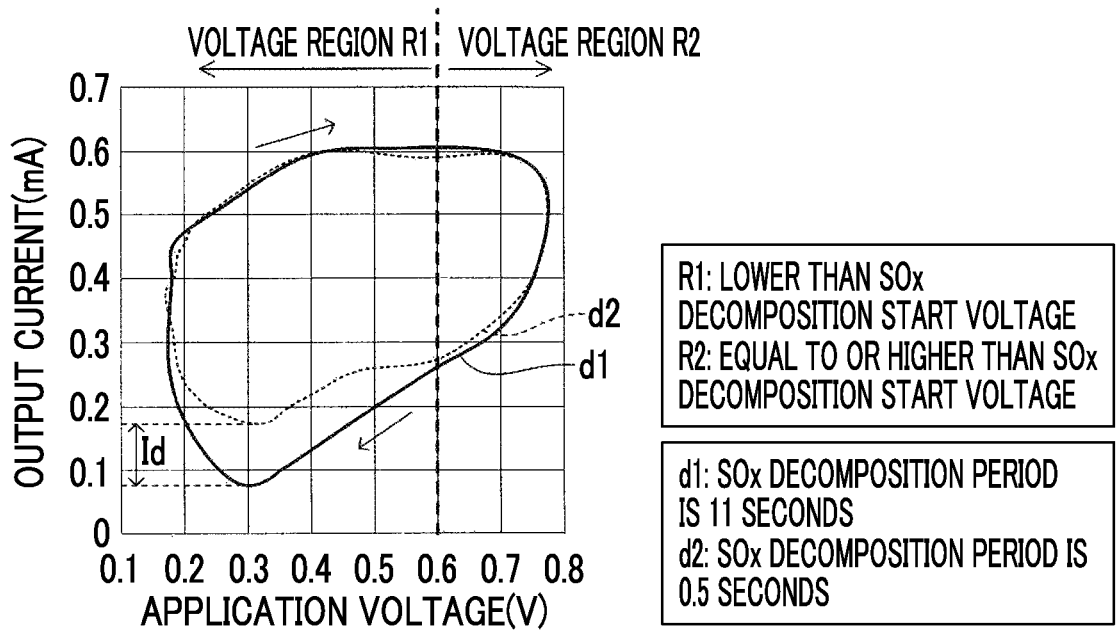

GAS DETECTION DEVICE

CROSS-REFERENCE TO RELATED APPLICATIONS

This application claims priority to Japanese Patent Application No. 2016-245413 filed on Dec. 19, 2016, which is incorporated herein by reference in its entirety.

BACKGROUND

1. Technical Field

The disclosure relates to a gas detection device that can determine whether a sulfur oxides concentration in an exhaust gas (a sample gas) of an internal combustion engine is equal to or higher than a predetermined value or detect the sulfur oxides concentration in the exhaust gas.

2. Description of Related Art

An air-fuel ratio sensor (hereinafter also referred to as an "A/F sensor") that acquires an air-fuel ratio (A/F) of an air-fuel mixture in a combustion chamber based on a concentration of oxygen ($O_2$) contained in an exhaust gas has been widely used to control an internal combustion engine. A limiting current type gas sensor is known as such a type of air-fuel ratio sensor.

A SOx concentration detection device (hereinafter also referred to as a "conventional device") that detects a concentration of sulfur oxides (hereinafter also referred to as "SOx") in an exhaust gas using such a limiting current type gas sensor has been proposed (for example, see Japanese Unexamined Patent Application Publication No. 2015-17931 (JP 2015-17931 A)).

The conventional device includes a sensing cell (an electrochemical cell) using an oxygen pumping effect of a solid electrolyte with oxygen ion conductivity. The conventional device generates oxide ions ($O^{2-}$) by applying a voltage across a pair of electrodes of the sensing cell to decompose gas components containing an oxygen atom (such as $O_2$, SOx, and $H_2O$ which are also referred to as "oxygen-containing components") in an exhaust gas. The conventional device detects characteristics of a current flowing between the electrodes of the sensing cell due to migration of oxide ions, which have been generated by decomposition of the oxygen-containing components, between the electrodes (an oxygen pumping effect).

Specifically, when a SOx concentration is detected, the conventional device performs an application voltage sweep. That is, the conventional device performs an application voltage sweep of stepping up an application voltage applied to the sensing cell from 0.4 V to 0.8 V and then stepping down the application voltage from 0.8 V to 0.4 V.

The conventional device calculates the SOx concentration using a difference between a reference current which is a "current (hereinafter referred to as an "electrode current" or an "output current") flowing between the electrodes of the sensing cell at a time point at which the application voltage reaches 0.8 V and a "peak value" which is a minimum value of the output current in a period in which the application voltage is stepped down from 0.8 V to 0.4 V.

SUMMARY

However, there is a high likelihood that the output current will change due to an influence of the oxygen-containing components other than SOx contained in the exhaust gas. For example, a decomposition voltage of water ($H_2O$) is substantially equal to a decomposition voltage of sulfur oxides or slightly higher than the decomposition voltage of sulfur oxides. A water concentration in the exhaust gas changes, for example, depending on an air-fuel ratio of an air-fuel mixture. Accordingly, it is difficult to detect an output current resulting from only decomposition of a SOx component without there being an influence from only decomposition of water on the output current. Accordingly, there is demand for accurately performing determination of whether a sulfur oxides concentration in the exhaust gas is equal to or higher than a predetermined value or detection of the sulfur oxides concentration in the exhaust gas using an "output current change due to only a SOx component without influence of oxygen-containing components other than SOx."

The disclosure provides a gas detection device (hereinafter also referred to as a "detection device") that can accurately perform determination of whether a sulfur oxides concentration in an exhaust gas is equal to or higher than a predetermined value or detection of the sulfur oxides concentration.

A gas detection device according to an aspect of the disclosure includes: an element portion which is disposed in an exhaust gas passage of an internal combustion engine, which includes an electrochemical cell including a solid electrolyte with oxide ion conductivity and a first electrode and a second electrode which are formed on surfaces of the solid electrolyte and a diffusion resistor formed of a porous material being able to transmit an exhaust gas flowing in the exhaust gas passage, and in which the exhaust gas flowing in the exhaust gas passage reaches the first electrode via the diffusion resistor; a voltage applying unit configured to apply a voltage across the first electrode and the second electrode; a current detecting unit configured to detect an output current which is a current flowing between the first electrode and the second electrode; and a measurement control unit configured to control an application voltage which is a voltage applied across the first electrode and the second electrode using the voltage applying unit, to acquire the output current using the current detecting unit, and to perform determination of whether sulfur oxides with a predetermined concentration or more is contained in the exhaust gas or detection of sulfur oxides concentration in the exhaust gas based on the acquired output current. The measurement control unit performs detection voltage control including first application voltage control, second application voltage control, and third application voltage control using the voltage applying unit. The first application voltage control is application voltage control of performing a step-up sweep of stepping up the application voltage from a first voltage, which is selected from a first voltage range which is higher than a lower limit voltage of a limiting current region in which the output current is a limiting current of oxygen and lower than a decomposition start voltage of sulfur oxides, to a second voltage which is higher than the decomposition start voltage of sulfur oxides. The second application voltage control is application voltage control of maintaining the application voltage to be equal to or higher than the decomposition start voltage of sulfur oxides over a predetermined voltage maintaining time from a time point at which the first application voltage control ends after the first application voltage control. The third application voltage control is application voltage control of performing step-down sweep of stepping down the application voltage from a voltage at a time point at which the second application voltage control ends to the first voltage at a predetermined step-down rate after the second application voltage control. The measurement control unit acquires a parameter, which has a correlation with a degree of change of the output current due to a current flowing between the first electrode and the second electrode due to return of sulfurs adsorbed on the first electrode to sulfur oxides by a reoxidation reaction in the first electrode when the application voltage is less than the decomposition start voltage of sulfur oxides during the step-down sweep, the degree of change of the output current increasing as the concentration of sulfur oxides in the exhaust gas increases, based on the output current, and performs determination of whether the concentration of sulfur oxides in the exhaust gas is equal to or higher than a predetermined value or detection of the concentration of sulfur oxides in the exhaust gas based on the acquired parameter.

According to the inventor's research, it was proved that an "output current change" which is not affected well by "oxygen-containing components other than sulfur oxides" due to return of "sulfurs adsorbed on the first electrode when a step-down sweep is performed" to sulfur oxides by reoxidation in the first electrode occurs. It was also proved that a degree of "output current change" changes greatly depending on a voltage drop per predetermined elapsed time (that is, a step-down rate) in the step-down sweep (see FIGS. 6A and 6B). A mechanism by which such a phenomenon occurs is thought to be as follows.

That is, sulfurs (a decomposition product of sulfur oxides) adsorbed on the first electrode by performing a step-up sweep is returned to sulfur oxides by reoxidation in the first electrode when a step-down sweep is performed. Decomposition products (for example, hydrogen which is a decomposition product of water) of oxygen-containing components other than sulfur oxides are not adsorbed on the first electrode when the step-up sweep is performed. Accordingly, the phenomenon that a decomposition product of oxygen-containing components other than sulfur oxides is returned to the oxygen-containing components by reoxidation in the first electrode does not occur substantially when the step-down sweep is performed.

Accordingly, the "output current change" which is caused due to return of sulfurs adsorbed on the first electrode to sulfur oxides by reoxidation in the first electrode when the step-down sweep is performed is not easily affected by oxygen-containing components other than sulfur oxides. That is, an "output current change" which is not easily affected by oxygen-containing components other than sulfur oxides occurs during the step-down sweep.

When a step-down rate (a sweeping rate) of the step-down sweep is lower than a certain rate, a reoxidation reaction of sulfur progresses continuously and slowly in the step-down sweep. Accordingly, hardly any degree of "output current change" appears even irrespective of the value of the sulfur oxides concentration.

On the other hand, when the step-down rate of the step-down sweep is higher than a certain rate, the application voltage decreases without such progress of the reoxidation reaction of sulfur in the step-down sweep. When the application voltage becomes a voltage in a certain voltage "range in which the reoxidation reaction of sulfur is activated (that is, a predetermined voltage range which is less than a decomposition start voltage of sulfur oxides)," the degree of output current change increases as the sulfur oxides concentration increases due to a rapid process of the reoxidation reaction of sulfur (an increase of a reoxidation reaction rate of sulfur, that is, a rapid increase of an occurrence frequency of the reoxidation reaction of sulfur). That is, a significant current change occurs in accurate detection of the sulfur oxides concentration.

Therefore, the step-down rate of the step-down sweep is set to a "rate at which the reoxidation reaction rate of sulfur increases rapidly from a time point at which the application voltage becomes a voltage in the predetermined voltage range less than the decomposition start voltage of sulfur oxides." Accordingly, an output current change which is not affected by oxygen-containing components other than sulfur oxides appears to be greater as the sulfur oxides concentration becomes higher.

The gas detection device according to the aspect of the disclosure acquires a parameter having a correlation with a "degree of change of the output current" due to the reoxidation reaction of sulfur based on the output current acquired by the detection voltage control.

In results of repeated study of the inventor, it could be seen that the "degree of change of the output current" due to the reoxidation reaction of sulfur varies depending on a sulfur oxidation decomposition period in which the application voltage is equal to or higher than the decomposition start voltage of sulfur oxides in the detection voltage control. Specifically, it could be seen that the "degree of change of the output current" due to the reoxidation reaction of sulfur is likely to become smaller as the sulfur oxides decomposition period becomes shorter and to become larger as the sulfur oxide decomposition period becomes longer. This is thought to be because as the sulfur oxides decomposition period becomes longer, an amount of sulfur oxides decomposed increases and thus the "degree of change of the output current" due to the reoxidation reaction of sulfur becomes larger.

In this regard, in the gas detection device according to the aspect of the disclosure, by performing the second application voltage control between the first application voltage control (the step-down sweep) and the third application voltage control (the step-up sweep), the sulfur oxides decomposition period becomes longer than that in a case in which the step-down sweep is performed continuously after the step-up sweep ends.

Accordingly, a difference depending on the sulfur oxides concentration appears distinctly in the parameter having a correlation with the "degree of change of the output current" acquired based on the output current when the detection voltage control is performed. As a result, it is possible to accurately perform detection of the sulfur oxides concentration (determination of whether the sulfur oxides concentration in the exhaust gas is equal to or higher than a predetermined value or detection of the sulfur oxides concentration in the exhaust gas). Particularly, even when the sulfur oxides concentration in the exhaust gas is low, the difference depending on the sulfur oxides concentration appears distinctly in the parameter having a correlation with the "degree of change of the output current." Accordingly, even when the SOx concentration in the exhaust gas is low, it is possible to accurately detect the sulfur oxides concentration.

In the aspect, the second application voltage control may be application voltage control of maintaining the application voltage at the second voltage over the voltage maintaining time.

According to this configuration, it is possible to accurately perform detection of the sulfur oxides concentration (determination of whether the sulfur oxides concentration in the exhaust gas is equal to or higher than a predetermined value or detection of the sulfur oxides concentration in the exhaust gas).

In the aspect, the measurement control unit may set the predetermined step-down rate to a rate at which the rate of the reoxidation reaction increases rapidly from a time point at which the application voltage becomes a voltage in a voltage range which is included in the first voltage range and is higher than the first voltage.

According to this configuration, the change of the output current which is not affected by oxygen-containing components other than sulfur oxides increases as the sulfur oxides concentration increases. Accordingly, by acquiring the parameter having a correlation with the degree of change of the output current, it is possible to accurately perform determination of whether the sulfur oxides concentration in the exhaust gas is equal to or higher than a predetermined value or detection of the sulfur oxides concentration in the exhaust gas based on the acquired parameter.

In the aspect, when it is determined that sulfur oxides with the predetermined concentration or more is not contained in the exhaust gas, the measurement control unit may perform the first application voltage control, corrected second application voltage control of maintaining the application voltage at a voltage equal to or higher than the decomposition start voltage of sulfur oxides over a voltage maintaining time which is longer than the voltage maintaining time in the detection voltage control which is performed for the determination, and the third application voltage control, may acquire the parameter again during the step-down sweep in the third application voltage control subsequent to the corrected second application voltage control, and may perform determination of whether the concentration of sulfur oxides in the exhaust gas is equal to or higher than a predetermined value lower than the predetermined value again based on the acquired parameter.

According to this configuration, even when the sulfur oxides concentration in the exhaust gas is low, the difference depending on the sulfur oxides concentration (the difference between when the sulfur oxides concentration is equal to or higher than a predetermined value and when the sulfur oxides concentration is lower than the predetermined value) appears distinctly in the parameter having a correlation with the "degree of change of the output current." Accordingly, it is possible to accurately perform determination of whether the sulfur oxides concentration in the exhaust gas is equal to or higher than a predetermined value which is lower than that in the previous determination (determination of whether the sulfur oxides concentration is equal to or higher than a sulfur oxides concentration lower than that in the previous determination of the sulfur oxides concentration).

In the aspect, the measurement control unit may perform the detection voltage control including the second application voltage control in which the voltage maintaining time is set to a first time to acquire the parameter as a first parameter, then may perform the detection voltage control including the second application voltage control in which the voltage maintaining time is set to a second time longer than the first time to acquire the parameter as a second parameter, may calculate a magnitude of a difference between the acquired first parameter and the acquired second parameter, and may perform determination of whether the concentration of sulfur oxides in the exhaust gas is equal to or higher than a predetermined value or detection of the concentration of sulfur oxides in the exhaust gas based on the calculated magnitude of the difference.

The magnitude of the difference between the first parameter and the second parameter varies depending on the sulfur oxides concentration and thus can serve as a parameter accurately indicating the sulfur oxides concentration, because an influence of an electrode state of a gas sensor (a current change due to capacitance and resistance of an electrode and capacitance and resistance of a solid electrolyte) is almost removed or reduced. The gas detection device can accurately detect the sulfur oxides concentration based on the magnitude of the difference.

In the aspect, when it is determined that sulfur oxides with the predetermined concentration or higher is not contained in the exhaust gas in the determination using the magnitude of the difference between the first parameter and the second parameter, the measurement control unit may perform the detection voltage control including the second application voltage control in which the voltage maintaining time is set to a third time longer than the second time to acquire the parameter as a third parameter, may calculate a magnitude of a difference between the acquired first parameter and the acquired third parameter, and may perform determination of whether the concentration of sulfur oxides in the exhaust gas is equal to or higher than a predetermined value lower than the predetermined value again based on the calculated magnitude of the difference.

According to this configuration, a sulfur oxides decomposition period of the detection voltage control which is performed again by the measurement control unit is set to be longer than that in the previous detection voltage control. Accordingly, even when the sulfur oxides concentration in the exhaust gas is low, the difference depending on the sulfur oxides concentration (the difference between when the sulfur oxides concentration is equal to or higher than a predetermined value and when the sulfur oxides concentration is lower than the predetermined value) appears distinctly in the magnitude of the difference. Accordingly, it is possible to accurately perform determination of whether the sulfur oxides concentration in the exhaust gas is equal to or higher than a predetermined value (whether the sulfur oxides concentration is equal to or lower than a sulfur oxides concentration which is lower than that in the previous determination of the sulfur oxides concentration).

In the above description, for the purpose of easy understanding of the disclosure, names which are used in an embodiment which will be described later are added in parentheses to elements of the disclosure corresponding to the embodiment. However, the elements of the disclosure are not limited to the embodiment defined by the names. Other objects, features, and advantages of the disclosure will be easily understood from the following description of the embodiment of the disclosure which will be described below with reference to the accompanying drawings.

BRIEF DESCRIPTION OF THE DRAWINGS

Features, advantages, and technical and industrial significance of exemplary embodiments of the disclosure will be described below with reference to the accompanying drawings, in which like numerals denote like elements, and wherein:

FIG. 3A is a timing chart illustrating an outline of an operation of the gas detection device according to the first embodiment of the disclosure;

FIG. 3B is a graph illustrating a waveform of an application voltage when SOx detection is performed;

FIG. 3C is a graph illustrating another waveform of the application voltage when SOx detection is performed;

FIG. 7A is a graph illustrating a relationship between an application voltage and an output current;

FIG. 7B is a graph illustrating a relationship between an application voltage and an output current;

DETAILED DESCRIPTION OF EMBODIMENTS

Figure 1:
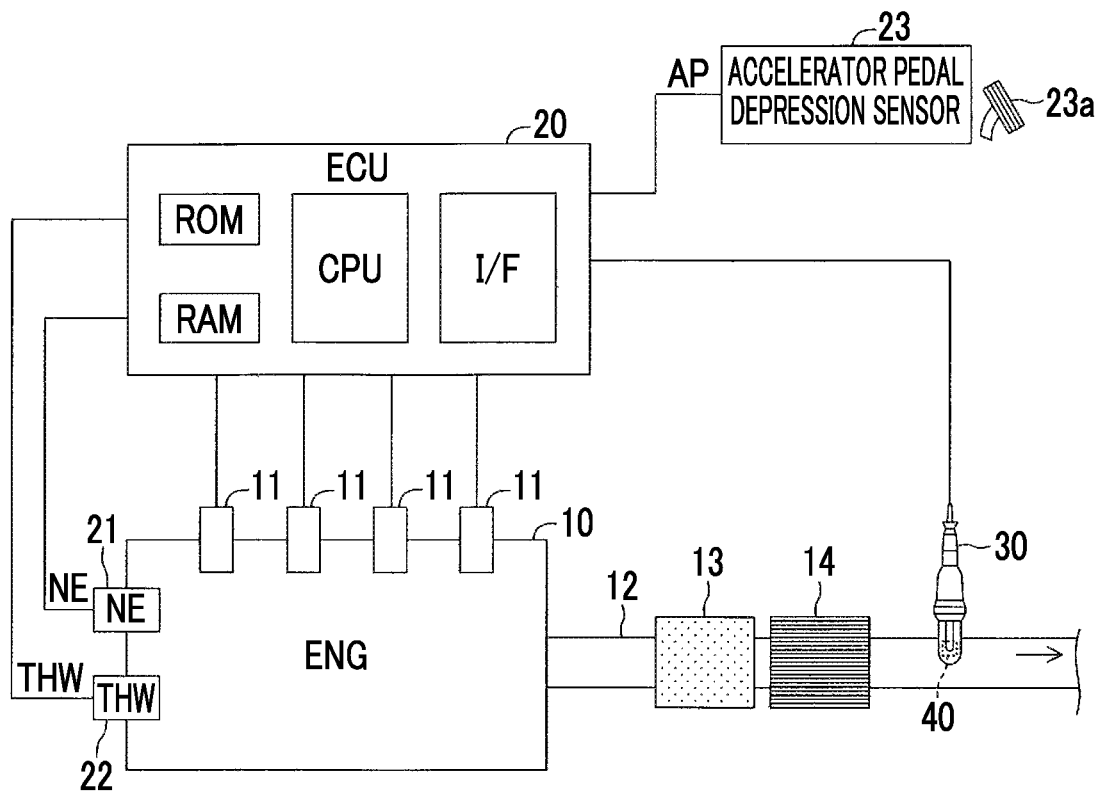
FIG. 1 is a diagram schematically illustrating a configuration of a gas detection device according to a first embodiment of the disclosure and an internal combustion engine to which the gas detection device is applied.

Hereinafter, gas detection devices according to embodiments of the disclosure will be described with reference to the accompanying drawings. In the drawings of the embodiments, the same or corresponding elements will be referenced by the same reference signs.

First Embodiment

A gas detection device according to a first embodiment of the disclosure (hereinafter also referred to as a "first detection device") will be described below. The first detection device is applied to an "internal combustion engine 10 illustrated in FIG. 1" mounted in a vehicle which is not illustrated.

The internal combustion engine 10 is a well-known diesel engine. The internal combustion engine 10 includes a combustion chamber which is not illustrated and a fuel injection valve 11. The fuel injection valve 11 is disposed in a cylinder head portion and injects fuel into the combustion chamber. The fuel injection valve 11 directly injects fuel into the combustion chamber in accordance with an instruction from an ECU 20 which will be described later. An exhaust pipe 12 is connected to an end of an exhaust gas manifold which is not illustrated and is connected to an exhaust port communicating with the combustion chamber which is not illustrated. The exhaust port, the exhaust gas manifold, and the exhaust pipe 12 constitute an exhaust gas passage in which exhaust gas discharged from the combustion chamber flows. A diesel oxidation catalyst (DOC) 13 and a diesel particulate filter (DPF) 14 are disposed in the exhaust pipe 12.

The DOC 13 is an exhaust gas purification catalyst. Specifically, the DOC 13 oxidizes unburned components (HC and CO) in the exhaust gas to purify the exhaust gas using precious metals such as platinum and palladium as a catalyst. That is, by the DOC 13, HC is oxidized to water and $CO_2$, and CO is oxidized to $CO_2$.

The DPF 14 is disposed downstream from the DOC 13. The DPF 14 is a filter that captures particulates in the exhaust gas. Specifically, the DPF 14 includes a plurality of pores formed by a porous material (for example, a diaphragm formed of cordierite which is a kind of ceramic). The DPF 14 captures particulates contained in the exhaust gas passing through the diaphragm on pore surfaces of the diaphragm.

The first detection device includes an electronic control unit (ECU) 20. The ECU 20 is an electronic control circuit including a microcomputer including a CPU, a ROM, a RAM, a backup RAM, and an interface (I/F) as a main constituent component. The CPU implements predetermined functions by executing instructions (routines) stored in the memory (ROM).

The ECU 20 is connected to various actuators of the internal combustion engine 10 (such as the fuel injection valve 11). The ECU 20 sends out a drive (instruction) signal to the actuators to control the internal combustion engine 10. The ECU 20 is connected to various sensors described below and receives signals from the sensors.

Engine Rotation Speed Sensor 21

An engine rotation speed sensor (hereinafter referred to as an "NE sensor") 21 measures a rotation speed (an engine rotation speed) NE of the internal combustion engine 10 and outputs a signal indicating the engine rotation speed NE.

Coolant Temperature Sensor 22

A coolant temperature sensor 22 is disposed in a cylinder block. The coolant temperature sensor 22 detects a temperature of a coolant (a coolant temperature THW) for cooling the internal combustion engine 10 and outputs a signal indicating the coolant temperature THW.

Accelerator Pedal Depression Sensor 23

An accelerator pedal depression sensor 23 detects an amount of operation of an accelerator pedal 23a (an accelerator depression amount) of the vehicle and outputs a signal indicating an accelerator pedal depression amount AP.

Gas Sensor 30

A gas sensor 30 is a one-cell limiting current type gas sensor and is disposed in an exhaust pipe 12 constituting an exhaust gas passage of the internal combustion engine 10. The gas sensor 30 is disposed downstream from the DOC 13 and the DPF 14 in the exhaust pipe 12.

Configuration of Gas Sensor

Figure 2:
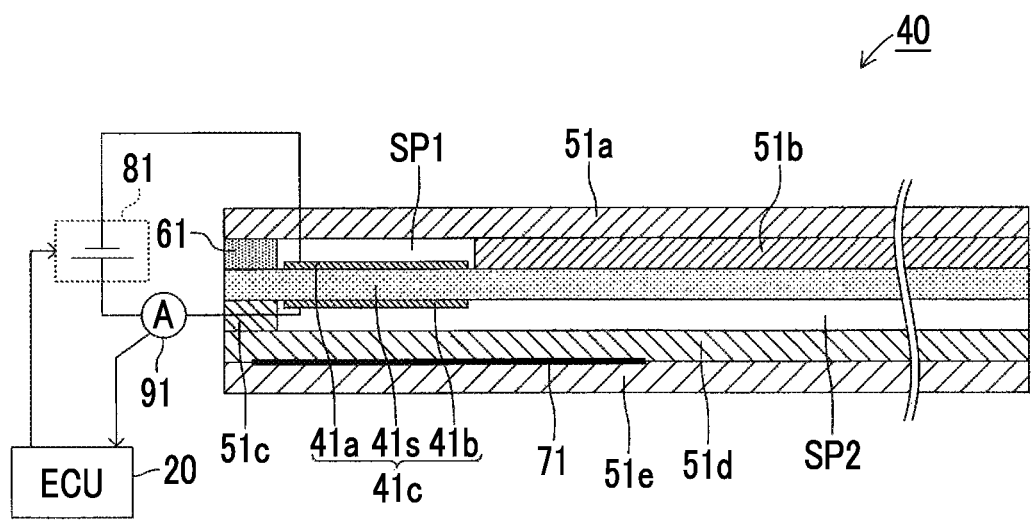
FIG. 2 is a cross-sectional view schematically illustrating an example of a configuration of a gas sensor element portion illustrated in FIG. 1.

A configuration of the gas sensor 30 will be described below with reference to FIG. 2. An element portion 40 included in the gas sensor 30 includes a solid electrolyte 41s, a first alumina layer 51a, a second alumina layer 51b, a third alumina layer 51c, a fourth alumina layer 51d, a fifth alumina layer 51e, a diffusion resistor portion (a diffusion rate control layer) 61, and a heater 71.

The solid electrolyte 41s is a thin plate member with oxide ion conductivity which contains zirconia. Zirconia forming the solid electrolyte 41s may contain an element such as scandium (Sc) and yttrium (Y).

Each of the first alumina layer 51a to the fifth alumina layer 51e is a dense (gas-non-transmitting) layer (a dense thin plate member) containing alumina.

The diffusion resistor portion 61 is a porous diffusion rate control layer and is a gas-transmitting layer (a thin plate member). The heater 71 is, for example, a thin plate member of cermet containing platinum (Pt) and ceramic (such as alumina) and is a heat emitter that emits heat with supply of electric power. The heater 71 is connected to a power source which is not illustrated and mounted in a vehicle via a lead wire which is not illustrated. An amount of heat emitted from the heater 71 can be changed by causing the ECU 20 to control an "amount of power supplied from the power source."

The layers of the element portion 40 are stacked from the bottom in the order of the fifth alumina layer 51e, the fourth alumina layer 51d, the third alumina layer 51c, the solid electrolyte 41s, the diffusion resistor portion 61, the second alumina layer 51b, and the first alumina layer 51a.

An internal space SP1 is formed by the first alumina layer 51a, the solid electrolyte 41s, the diffusion resistor portion 61, and the second alumina layer 51b. An exhaust gas of the internal combustion engine 10 as a sample gas is introduced into the internal space SP1 via the diffusion resistor portion 61. That is, the internal space SP1 communicates with the inside of the exhaust pipe 12 of the internal combustion engine 10 via the diffusion resistor portion 61. Accordingly, an exhaust gas in the exhaust pipe 12 is introduced as a sample gas into the internal space SP1. A first air introduction passage SP2 is formed by the solid electrolyte 41s, the third alumina layer 51c, and the fourth alumina layer 51d and is open to the atmosphere outside the exhaust pipe 12.

The first electrode 41a is fixed to one surface of the solid electrolyte 41s (specifically, the surface of the solid electrolyte 41s defining the internal space SP1). The first electrode 41a is a negative electrode. The first electrode 41a is a porous cermet electrode containing platinum (Pt) as a main component.

The second electrode 41b is fixed to the other surface of the solid electrolyte 41s (specifically, the surface of the solid electrolyte 41s defining the first air introduction passage SP2). The second electrode 41b is a positive electrode. The second electrode 41b is a porous cermet electrode containing platinum (Pt) as a main component.

The first electrode 41a and the second electrode 41b are disposed to face each other with the solid electrolyte 41s interposed therebetween. That is, the first electrode 41a, the second electrode 41b, and the solid electrolyte 41s constitute an electrochemical cell 41c having an oxygen discharge capability based on an oxygen pumping effect. The electrochemical cell 41c is heated to an activation temperature by the heater 71.

The layers including the solid electrolyte 41s and the first to fifth alumina layers 51a to 51e are formed in a sheet shape, for example, using a doctor blade method or an extrusion molding method. The first electrode 41a, the second electrode 41b, wires for supplying power to the electrodes, and the like are formed, for example, using a screen printing method. By stacking and baking such sheets as described above, the element portion 40 having the above-mentioned structure is integrally formed.

A material of the first electrode 41a is not limited to the above-mentioned materials and can be selected, for example, from materials containing a platinum group element such as platinum (Pt), rhodium (Rh), or palladium (Pd) or an alloy thereof as a main component. The material of the first electrode 41a is not particularly limited as long as SOx contained in a sample gas introduced into the internal space SP1 via the diffusion resistor portion 61 can be reductively decomposed when a voltage equal to or higher than a decomposition start voltage (specifically, a voltage of about 0.6 V or more) of SOx is applied between the first electrode 41a and the second electrode 41b.

The gas sensor 30 includes a power supply circuit 81 and an ammeter 91. The power supply circuit 81 and the ammeter 91 are connected to the ECU 20.

The power supply circuit 81 is configured to apply a predetermined voltage (hereinafter also referred to as an "application voltage Vm") across the first electrode 41a and the second electrode 41b such that the potential of the second electrode 41b is higher than the potential of the first electrode 41a. The power supply circuit 81 can change the application voltage Vm under the control of the ECU 20.

The ammeter 91 measures an output current (an electrode current) Im which is a current flowing between the first electrode 41a and the second electrode 41b (that is, a current flowing in the solid electrolyte 41s) and outputs the measured value to the ECU 20.

Outline of Operation

An outline of an operation which is performed by the first detection device will be described below. The first detection device is configured to detect an oxygen concentration in an exhaust gas (a sample gas) discharged from the internal combustion engine 10. The first detection device is configured to detect an air-fuel ratio (A/F) of an air-fuel mixture in the combustion chamber of the internal combustion engine 10 based on the oxygen concentration in the exhaust gas. Hereinafter, the air-fuel ratio of the air-fuel mixture in the combustion chamber of the internal combustion engine 10 is also referred to as an "air-fuel ratio A/F of an engine."

The first detection device is configured to detect a SOx concentration by determining whether the SOx concentration in the exhaust gas is equal to or higher than a predetermined value (which may be referred to as "SOx concentration determination." Since several seconds is required from start of detection of SOx concentration to end of detection thereof, the first detection device is configured to detect a SOx concentration in a state in which the air-fuel ratio A/F of an engine is stable (when an engine 10 can operate such that the air-fuel ratio A/F of the engine is stabilized). An arbitrary concentration which is greater than 0% and corresponds to a desired detection level is selected as the predetermined value.

Specifically, as illustrated in FIG. 3A, at time t0 which is a time point at which the internal combustion engine 10 is started, the first detection device starts control of the heater 71 such that the solid electrolyte 41s is heated by the heater 71. Accordingly, the temperature of the solid electrolyte 41s increases to a predetermined temperature equal to or higher than a temperature (hereinafter also referred to as an "activation temperature") at which the solid electrolyte 41s exhibits oxide ion conductivity.

At time t1, when the temperature of the solid electrolyte 41s (a sensor element temperature) is equal to or higher than the activation temperature and the gas sensor 30 enters a sensor-activated state, the first detection device starts a process of detecting an oxygen concentration in the exhaust gas and acquiring the air-fuel ratio A/F of the engine based on the oxygen concentration. At time td which is a time point between time t0 and time t1, the first detection device starts application of an oxygen concentration (A/F) detection voltage (for example, 0.4 V) which is suitable for detecting the oxygen concentration across the first electrode 41a and the second electrode 41b. That is, the first detection device sets the application voltage Vm to the oxygen concentration detection application voltage Vaf. When the temperature of the solid electrolyte 41s is equal to or higher than the activation temperature and the application voltage Vm is set to the oxygen concentration detection application voltage Vaf, oxygen molecules are decomposed and the oxygen pumping effect is exhibited, but gas of oxygen-containing components (which contains SOx) other than oxygen are not decomposed.

From time t1, the first detection device monitors the air-fuel ratio A/F of the engine by continuously detecting the oxygen concentration. At time t2, when SOx detection conditions are satisfied (that is, when the air-fuel ratio A/F of the engine is stable and other conditions which will be described later are satisfied), the first detection device starts application voltage control (referred to as "SOx detection voltage control") for performing a SOx concentration detecting process. In a period from time t2 to immediately before time t3, the first detection device detects the SOx concentration in the exhaust gas by acquiring a parameter indicating the SOx concentration in the exhaust gas (referred to as a "SOx detection parameter" which is a parameter varying depending on the SOx concentration) by the SOx detection voltage control and determining whether the SOx concentration in the exhaust gas is equal to or higher than a predetermined value using the parameter.

The first detection device performs the SOx detection voltage control in which first application voltage control, second application voltage control, and third application voltage control are performed in this order.

First Application Voltage Control

This is a step-up sweep of slowly stepping up the application voltage Vm from a first voltage V1 (specifically, 0.4 V) lower than a SOx decomposition start voltage to a second voltage V2 (specifically, 0.8 V) higher than the SOx decomposition start voltage.

Second Application Voltage Control

This is application voltage control of maintaining the application voltage Vm at a "voltage in a voltage range higher than the SOx decomposition start voltage" from a time point at which the first application voltage control (the step-up sweep) ends to a time point at which the third application voltage control (a step-down sweep to the first voltage V1) starts. Specifically, the first detection device performs application voltage control of maintaining the application voltage Vm at a "voltage equal to or higher than the SOx decomposition start voltage" up to a time point at which the step-down sweep to the first voltage V1 (the third application voltage control) starts by maintaining the application voltage Vm at the same voltage (specifically, 0.8 V) over a predetermined voltage maintaining period from a time point at which the first application voltage control (the step-up sweep) ends. So long as the application voltage Vm can be maintained at a "voltage equal to or higher than the SOx decomposition start voltage," "control of slowly stepping up the application voltage Vm," "control of slowly stepping down the application voltage Vm," or both thereof may be performed in addition to the "control of maintaining the application voltage Vm at the same voltage." So long as the application voltage Vm can be maintained at a "voltage equal to or higher than the SOx decomposition start voltage," "control of slowly stepping up the application voltage Vm," "control of slowly stepping down the application voltage Vm," or both thereof may be performed instead of the "control of maintaining the application voltage Vm at the same voltage."

Third Application Voltage Control

This is a step-down sweep of slowly stepping down the application voltage Vm from a voltage (that is, a voltage at a time point at which the step-down sweep to the first voltage V1 starts (specifically, 0.8 V)), which is a voltage higher than the SOx decomposition start voltage, at a time point at which the second application voltage control ends to the first voltage V1 (specifically, 0.4 V). A sweeping rate of the step-down sweep is set to a "predetermined sweeping rate" which will be described later.

In the SOx detection voltage control, the application voltage Vm at the time point at which the first application voltage control starts and the application voltage Vm at the time point at which the third application voltage control ends may not be equal to each other. The application voltage Vm at the time point at which the first application voltage control ends and the application voltage Vm at the time point at which the third application voltage control starts may not be equal to each other.

At time t3, when SOx concentration detection using the SOx detection voltage control ends, the first detection device restarts the process of detecting the air-fuel ratio A/F of the engine. That is, the first detection device sets the application voltage Vm to the oxygen concentration detection application voltage Vaf (0.4 V) at time t3.

A/F Detection

An operation for detecting the air-fuel ratio A/F of the engine will be described below. When the gas sensor 30 is in the sensor-activated state, the first detection device sets the application voltage Vm to the oxygen concentration detection application voltage Vaf (for example, 0.4 V) such that the first electrode 41a has a low potential and the second electrode 41b has a high potential to acquire the air-fuel ratio A/F of the engine. That is, the first electrode 41a functions as a negative electrode and the second electrode 41b functions as a positive electrode. The oxygen concentration detection application voltage Vaf is set to a voltage which is equal to or higher than a voltage (a decomposition start voltage) at which decomposition of oxygen ($O_2$) in the first electrode 41a is started and less than a decomposition start voltage of oxygen-containing components other than oxygen. Accordingly, oxygen contained in the exhaust gas is reductively decomposed into oxide ions ($O^2$) in the first electrode 41a.

The oxide ions are transmitted to the second electrode 41b via the solid electrolyte 41s and are changed to oxygen ($O_2$) and are discharged to the atmosphere via the first air introduction passage SP2. As described above, the migration of oxygen due to transmission of oxide ions from the negative electrode (the first electrode 41a) to the positive electrode (the second electrode 41b) via the solid electrolyte 41s is referred to as an "oxygen pumping effect."

Due to the transmission of oxide ions due to the oxygen pumping effect, a current flows between the first electrode 41a and the second electrode 41b. The current flowing between the first electrode 41a and the second electrode 41b is referred to as an "output current Im (or an electrode current Im)." In general, the output current Im has a trend of increasing as the application voltage Vm increases. However, since a flow rate of the exhaust gas reaching the first electrode 41a is limited by the diffusion resistor portion 61, a consumption rate of oxygen due to the oxygen pumping effect is higher than a feed rate of oxygen to the first electrode 41a. That is, the reductive decomposition reaction of oxygen in the first electrode 41a (the negative electrode) is in a diffusion rate controlled state.

When the reductive decomposition reaction of oxygen in the first electrode 41a is in a diffusion rate controlled state, the output current Im does not increase but is substantially constant in spite of an increase of the application voltage Vm. Such characteristics are referred to as "limiting current characteristics." A range of the application voltage in which the limiting current characteristics are exhibited (measured) is referred to as a "limiting current region." The output current Im in the limiting current region is referred to as a "limiting current." The magnitude of the limiting current for oxygen (a limiting current value) corresponds to a feed rate of oxygen to the first electrode 41a (the negative electrode). Since the flow rate of the exhaust gas reaching the first electrode 41a is kept constant by the diffusion resistor portion 51 as described above, the feed rate of oxygen to the first electrode 41a corresponds to the concentration of oxygen contained in the exhaust gas.

Accordingly, in the gas sensor 30, the output current (the limiting current) Im when the application voltage Vm is set to the "oxygen concentration detection application voltage Vaf which is a predetermined voltage in the limiting current region of oxygen (specifically, 0.4 V)" corresponds to the concentration of oxygen contained in the exhaust gas. In this way, the first detection device detects the concentration of oxygen contained in the exhaust gas as a sample gas using the limiting current characteristics of oxygen.

That is, the first detection device stores a relationship between the limiting current of oxygen and the oxygen concentration in the ROM in advance and detects the oxygen concentration in the exhaust gas based on the relationship and the detected limiting current of oxygen. On the other hand, the air-fuel ratio A/F of the engine and the oxygen concentration in the exhaust gas have a one-to-one correspondence relationship. Accordingly, the first detection device stores the relationship in the ROM in advance and detects the air-fuel ratio A/F of the engine based on the relationship and the detected oxygen concentration. The first detection device may store a relationship between the limiting current of oxygen and the air-fuel ratio A/F of the engine in the ROM in advance and acquire the air-fuel ratio A/F of the engine based on the relationship and the detected limiting current of oxygen.

Detection Principle of SOx Concentration Detection

A method of detecting a SOx concentration in an exhaust gas will be described below. The above-mentioned oxygen pumping effect also occurs for oxygen-containing components such as "SOx (sulfur oxides) and $H_2O$ (water)" containing an oxygen atom in a molecule. That is, when a voltage equal to or higher than the decomposition start voltages of the compounds is applied across the first electrode 41a and the second electrode 41b, the compounds are reductively decomposed to produce oxide ions. The oxide ions are conducted from the first electrode 41a to the second electrode 41b due to the "oxygen pumping effect." Accordingly, an output current Im flows between the first electrode 41a and the second electrode 41b.

However, the concentration of SOx contained in the exhaust gas is very low and a current due to decomposition of SOx is very small. A current due to decomposition of oxygen-containing components (such as water and carbon dioxides) other than SOx also flows between the first electrode 41a and the second electrode 41b. Accordingly, it is difficult to accurately detect only the output current due to SOx.

Therefore, as results of intensive research, the inventor of the disclosure acquired the knowledge that it is possible to accurately detect the SOx concentration by performing an application voltage sweep using a step-up sweep and a "step-down sweep at a predetermined sweeping rate" as one cycle at the time of detecting the SOx.

The step-up sweep is a process of slowly stepping up the application voltage Vm from the first voltage V1 to the second voltage V2. The step-down sweep is a process of slowly stepping down the application voltage Vm from the second voltage V2 to the first voltage V1. The first voltage V1 and the second voltage V2 are the potential of the second electrode 41b relative to the potential of the first electrode 41a and have a positive voltage value.

Figure 4:
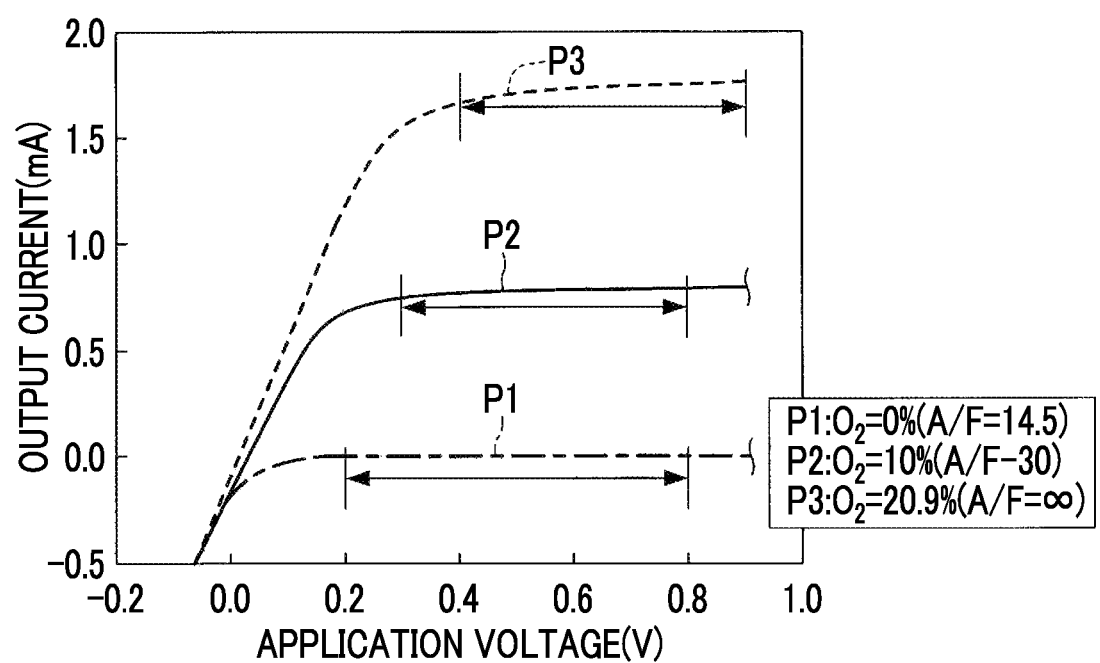
FIG. 4 is a graph illustrating a relationship between an A/F of an air-fuel mixture in a combustion chamber and a limiting current region of oxygen.

The first voltage V1 is set to a voltage in a voltage range (hereinafter also referred to as a "first voltage range") which is lower than the SOx decomposition start voltage (about 0.6 V) and higher than a minimum value of the application voltage Vm in the limiting current region of oxygen. As illustrated in FIG. 4, since the minimum value of the application voltage Vm in the limiting current region of oxygen (in the voltage range indicated by a bidirectional arrow) depends on the air-fuel ratio A/F of the engine, a lower limit value of the first voltage range may be changed depending on the air-fuel ratio A/F of the engine. Specifically, the lower limit value of the first voltage range is a voltage in a range of 0.15 V to 0.45 V and an upper limit voltage of the first voltage range is 0.6 V. That is, the first voltage V1 is a voltage which is selected in a range equal to or higher than 0.15 V and lower than 0.6 V.

The second voltage V2 is set to a voltage in a voltage range (hereinafter also referred to as a "second voltage range") which is higher than the SOx decomposition start voltage (about 0.6 V) and lower than an upper limit value (2.0 V) of a voltage at which the solid electrolyte 41s does not break down. That is, the second voltage V2 is a voltage which is selected in a range higher than 0.6 V and equal to or lower than 2.0 V.

Figure 5A:
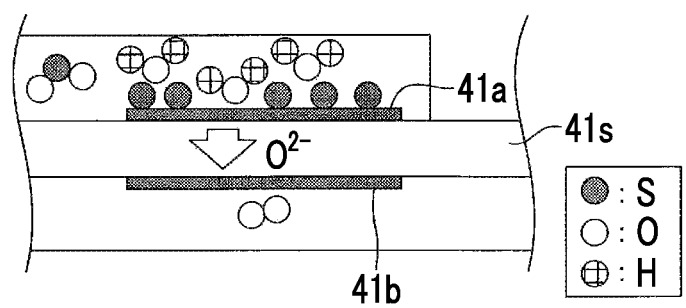
FIG. 5A is a diagram schematically illustrating a decomposition reaction of SOx which occurs in the element portion.

In a period in which the step-up sweep is performed, the application voltage Vm applied across the first electrode 41a and the second electrode 41b becomes equal to or higher than the SOx decomposition start voltage, and SOx contained in the exhaust gas is reductively decomposed into S and $O^2$ in the first electrode 41a (the negative electrode) as illustrate d in FIG. 5A. As a result, a reductive decomposition product (S (sulfur)) of SOx is adsorbed on the first electrode 41a (the negative electrode).

Figure 5B:
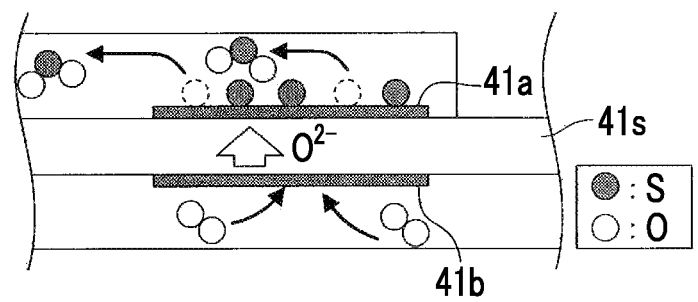
FIG. 5B is a diagram schematically illustrating a reoxidation reaction of sulfur which occurs in the element portion.

In a period in which the step-down sweep is performed, when the application voltage Vm becomes lower than the SOx decomposition start voltage, a reaction in which S and $O^{2-}$ adsorbed on the first electrode 41a (the negative electrode) react with each other to produce SOx (hereinafter also referred to as a "reoxidation reaction of S (sulfur)") occurs as illustrated in FIG. 5B. At this time, the output current Im changes as will be described later due to the "reoxidation reaction of S." The change of the output current Im due to the "reoxidation reaction of S" is referred to as a "reoxidation current change."

According to the research of the inventor, it was proved that a significant reoxidation current change may not appear in the SOx concentration detection depending on the sweeping rate of the step-down sweep. This will be described below with reference to FIGS. 6A and 6B.

Figure 6A:
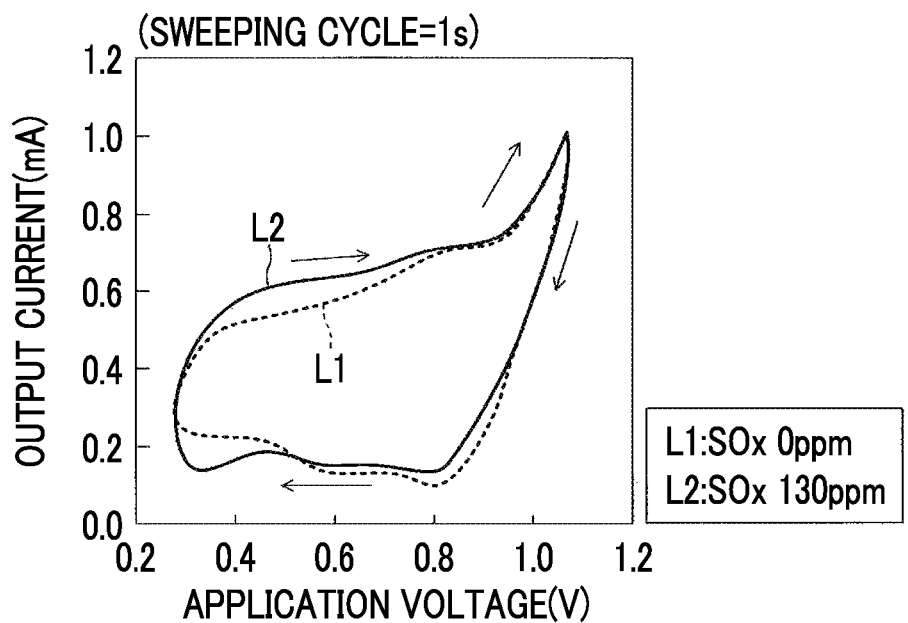
FIG. 6A is a graph illustrating a relationship between an application voltage and an output current.
Figure 6B:
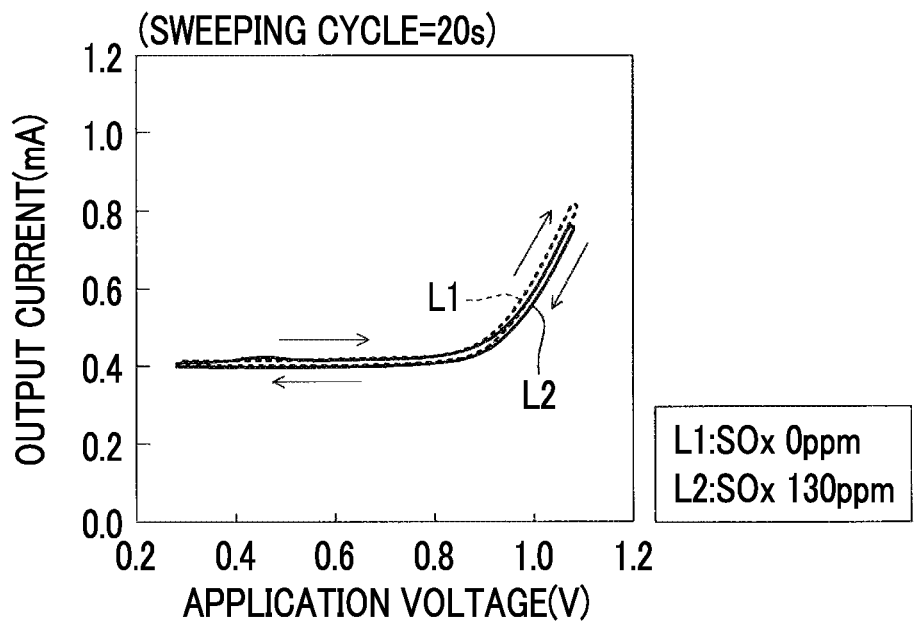
FIG. 6B is a graph illustrating a relationship between an application voltage and an output current.

FIG. 6A is a graph schematically illustrating a relationship between the application voltage Vm and the output current Im when the application voltage sweep is performed with a sweeping cycle time (that is, a sum of a time required for the step-up sweep and the time required for the step-down sweep, a cycle time of the application voltage sweep) set to 1 second. FIG. 6B is a graph schematically illustrating a relationship between the application voltage Vm and the output current Im when the application voltage sweep is performed at a sweeping rate (with a sweeping cycle time of 20 seconds) which is lower than that in the example illustrated in FIG. 6A.

In a result of comparison between both examples, a difference (a difference in current value) between the "output current Im when the SOx concentration in a sample gas is 0 ppm" indicated by a line L1 and the "output current Im when the SOx concentration in the sample gas is 130 ppm" indicated by a line L2 in a voltage range lower than the SOx decomposition start voltage (0.6 V) appears more distinctly in the example illustrated in FIG. 6A in which the sweeping rate of the application voltage sweep is higher than that in the example illustrated in FIG. 6B. That is, in the example illustrated in FIG. 6A, a significant current change (the reoxidation current change) appears in the SOx concentration detection. The mechanism by which such a phenomenon occurs is thought to be as follows.

That is, when the sweeping rate is set to be lower than a predetermined rate, the reoxidation reaction of S progresses continuously and slowly in the step-down sweep and thus a significant reoxidation current change does not appear. On the other hand, when the sweeping rate is set to be higher than a predetermined sweeping rate, the reoxidation reaction of S does not progress as much and the application voltage Vm decreases in the step-down sweep. When the application voltage Vm becomes a voltage in a "voltage range in which the reoxidation reaction of S is activated," the reoxidation reaction of S progresses rapidly. Accordingly, a significant current change appears in the SOx concentration detection.

In this way, depending on the sweeping rate when the step-down sweep is performed, a significant current change may appear or may not appear in the SOx concentration detection. Accordingly, in the step-down sweep, it is necessary to set the sweeping rate to a predetermined rate at which a significant current change indicating the reoxidation current change appears.

In the first detection device, the predetermined rate is set to an appropriate rate at which a significant current change indicating the reoxidation current change appears by preliminary experiment.

According to the experiment, for example, it was proved that when a voltage of a sinusoidal waveform illustrated in FIG. 3B is applied across the first electrode 41a and the second electrode 41b, the sweeping rate may be set to a rate at which a frequency F in a predetermined range (typically a range of 0.1 Hz to 5 Hz) is obtained. The lower limit value of the frequency F in the predetermined range is determined from a point of view that a significant signal difference (the reoxidation current change) is not obtained in the SOx concentration detection when the frequency is lower than the lower limit value. The upper limit value of the frequency F in the predetermined range is determined from a point of view that a degree of contribution from other causes of a current change (specifically, a capacitance of the solid electrolyte 41s or the like) other than the SOx concentration increases when the frequency is higher than the upper limit value.

On the other hand, according to the experiment, it was also proved that when a voltage of a non-sinusoidal waveform resulting from charging/discharging of a capacitor is applied across the first electrode 41a and the second electrode 41b as illustrated in FIG. 3C, the sweeping rate may be set to a rate at which a response time T1 of a voltage switching waveform is in a predetermined range (typically, a range of 0.1 sec to 5 sec). The response time T1 is a time required for the application voltage Vm to change from a lower limit voltage of the predetermined range to an upper limit voltage thereof or vice versa. The lower limit voltage and the upper limit voltage of the predetermined range of the response time T1 are determined to be appropriate values from the same point of view as in a case in which the frequency F (the predetermined frequency) is determined using the voltage of a sinusoidal waveform as the application voltage.

When the predetermined ranges of the frequency F and the response time T1 are converted into a time required for the step-down sweep (a time until the application voltage changes from the second voltage V2 to the first voltage V1), the predetermined ranges are converted into ranges of 0.1 sec to 5 sec. In some embodiments, the time ranges from 0.1 sec to 5 sec.

It was proved that the reoxidation current change mainly depends on the SOx concentration in an exhaust gas as a sample gas. In other words, there is a low likelihood that the reoxidation current change is affected by a "gas (for example, water) of oxygen-containing components other than sulfur oxides (SOx)" in the exhaust gas. That is, when the step-up sweep is performed, "decomposition products (for example, hydrogen which is a decomposition product of water) of other components (oxygen-containing components) other than sulfur oxides" are not adsorbed on the first electrode 41a. Accordingly, a phenomenon that decomposition products of "oxygen-containing components other than sulfur oxides" undergo a reoxidation reaction in the first electrode 41a and are returned to the oxygen-containing components does not substantially occur in a period in which the step-down sweep is performed.

Accordingly, the "output current change" occurring due to return of sulfurs adsorbed on the first electrode 41a to sulfur oxides by reoxidation in the first electrode 41a in the step-down sweep is not easily affected by oxygen-containing components other than sulfur oxides. That is, the "output current change" which is not easily affected by oxygen-containing components other than sulfur oxides occurs.

It was proved that the "output current change (the reoxidation current change)" occurs such that characteristics that the output current Im decreases as the SOx concentration in the exhaust gas (the sample gas) increases are exhibited. That is, when a reoxidation reaction of sulfur occurs, oxide ions are consumed in the first electrode 41*a* as illustrated in FIG. 5B and thus an amount of oxide ions (for example, oxide ions produced by decomposition of oxygen molecules) migrating from the first electrode 41*a* to the second electrode 41*b* decreases. Accordingly, the output current Im decreases. As the SOx concentration in the exhaust gas increases, an amount of sulfur adsorbed on the first electrode 41*a* in the step-up sweep increases and thus an amount of oxide ions consumed by reaction with sulfur also increases particularly in the first electrode 41*a* in the step-down sweep. As a result, an amount of oxide ions migrating from the first electrode 41*a* to the second electrode 41*b* also decreases. Accordingly, as the SOx concentration in the exhaust gas increases, the output current Im decreases.

From the above description, it can be understood "that it is possible to accurately detect the SOx concentration without being affected by a gas (for example, water) of oxygen-containing components other than SOx in the exhaust gas using the reoxidation current change." That is, it can be understood that it is possible to accurately detect the SOx concentration using a degree of decrease of the output current Im in the "reoxidation current change" in which the output current Im decreases as the SOx concentration in the exhaust gas increases.

As further study results by the inventor of the disclosure, it could be seen that the degree of decrease of the output current Im in the "reoxidation current change" varies depending on a period (referred to as a "SOx decomposition period") in which the application voltage Vm is equal to or higher than the SOx decomposition start voltage in the application voltage sweep. Specifically, it could be seen that the degree of decrease of the output current Im in the "reoxidation current change" decreases as the SOx decomposition period is shortened and increases as the SOx decomposition period is extended. This is thought to be because as the SOx decomposition period is extended, an amount of sulfur oxides decomposed increases and thus the degree of decrease of the output current Im in the "reoxidation current change" also increases.

FIG. 7A illustrates V-I characteristics when the application voltage control is performed under an experiment condition that the SOx concentration in the exhaust gas is low. FIG. 7B illustrates V-I characteristics when the application voltage control is performed under an experiment condition that the SOx concentration in the exhaust gas is higher than that in FIG. 7A. A line c1 and a line d1 indicate V-I characteristics when the application voltage Vm is controlled as indicated by a solid line in FIG. 8A (that is, when the SOx decomposition period is long (specifically, 11 seconds)). A line c2 and a line d2 indicate V-I characteristics when the application voltage Vm is controlled as indicated by a dotted line in FIG. 8A (that is, when the SOx decomposition period is short (specifically, 0.5 seconds)).

Comparing the V-I characteristics indicated by the line c1 with the V-I characteristics indicated by the line c2 and comparing the V-I characteristics indicated by the line d1 with the V-I characteristics indicated by the line d2, it can be seen that the degree of decrease of the output current Im in the "reoxidation current change" appearing in a voltage region R1 lower than the SOx decomposition start voltage decreases as the SOx decomposition period is shortened.

When the SOx decomposition period is excessively short and the degree of decrease of the output current Im in the "reoxidation current change" decreases, the difference in the output current depending on the SOx concentration required for accurate detection of the SOx concentration does not appear well. Accordingly, detection accuracy of the SOx concentration deteriorates. Particularly, when the SOx concentration in the exhaust gas is low, the degree of decrease of the output current Im in the "reoxidation current change" varying depending on the SOx concentration in the exhaust gas is small and thus the difference in the output current depending on the SOx concentration appears less than in a case in which the SOx concentration is high. As a result, the detection accuracy of the SOx concentration deteriorates further.

On the other hand, when the application voltage sweep for detecting the SOx concentration is performed and the "SOx decomposition period (a period in which the application voltage Vm is a voltage equal to or higher than the SOx decomposition start voltage (a voltage region R2))" is set to be longer, the difference in the output current depending on the SOx concentration can appear more distinctly (see comparison of the line c1 with the line d1). Particularly, when the SOx concentration is low, the difference in the output current depending on the SOx concentration can appear distinctly. As a result, it is possible to accurately detect the SOx concentration.

Figure 8A:
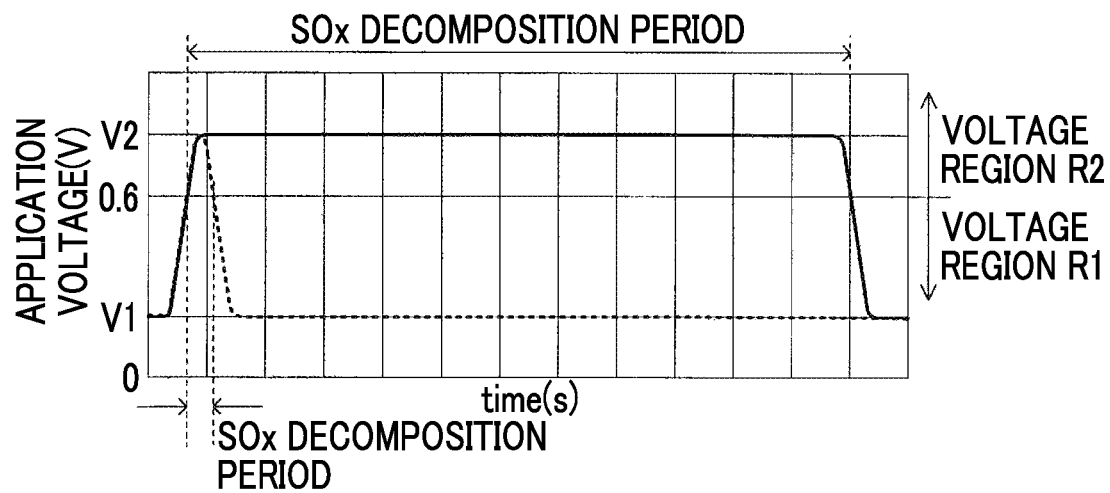
FIG. 8A is a graph illustrating a relationship between an elapsed time and an application voltage.
Figure 8B:
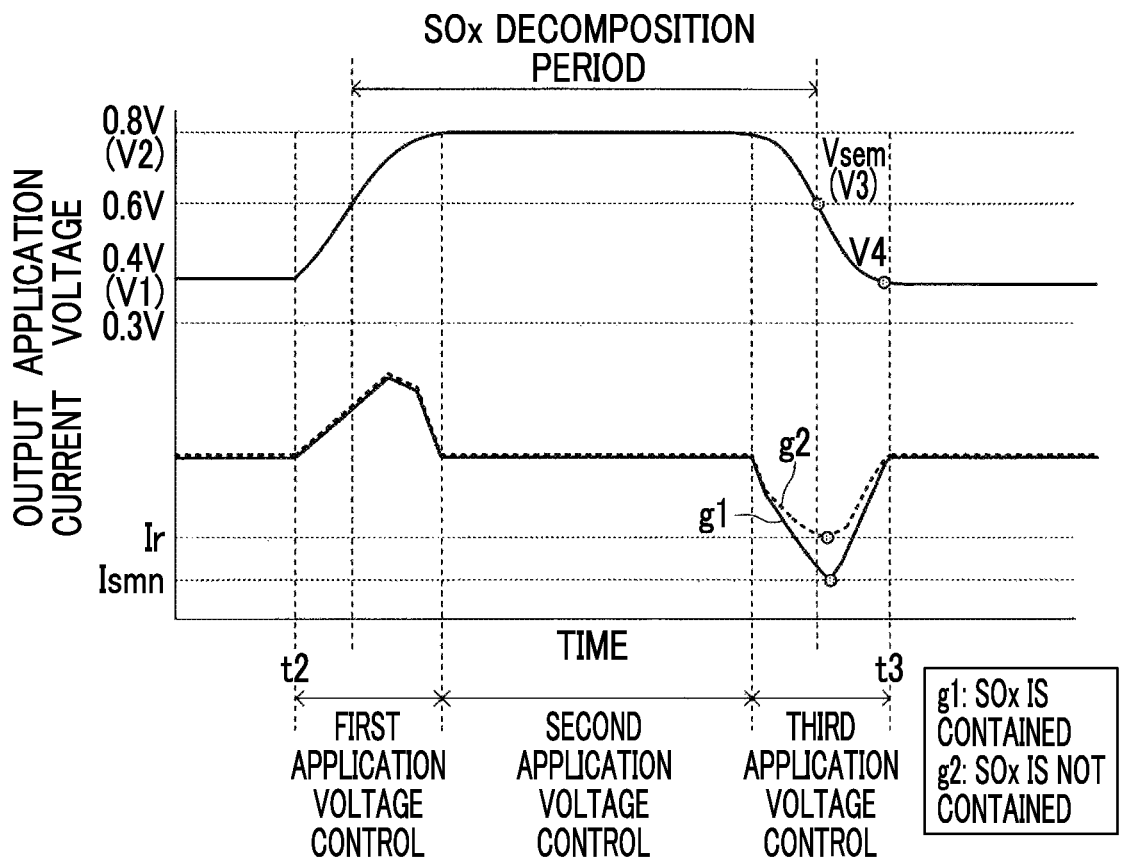
FIG. 8B is a graph illustrating a relationship between an elapsed time and each of an application voltage and an output current.

Therefore, as illustrated in FIG. 8B, the first detection device performs the second application voltage control of maintaining the application voltage Vm at a voltage equal to or higher than the SOx decomposition start voltage over a predetermined voltage maintaining time between the first application voltage control (the step-up sweep) and the third application voltage control (the step-down sweep). Accordingly, the period (the SOx decomposition period) in which the application voltage Vm is maintained at a voltage equal to or higher than the SOx decomposition start voltage is longer than that when the step-down sweep is continuously performed after the step-up sweep ends (for example, when the application voltage control indicated by a dotted line in FIG. 8A is performed) and is equal to or greater than a predetermined time.

In some embodiments, a time (for example, equal to or greater than 1 sec, equal to or greater than 1 sec and less than 60 sees) equal to or greater than such a time in which a difference depending on the SOx concentration (a difference between when the SOx concentration is equal to or higher than a predetermined value and when the SOx concentration is less than the predetermined value) appears in the SOx detection parameter such that the SOx concentration can be determined is selected as the predetermined time. The predetermined time changes depending on a desired SOx concentration detection level (the magnitude of the predetermined value of the criterion for SOx determination) and a time with an arbitrary length can be determined by experiment or the like.

Parameter for Detecting Reoxidation Current Change (SOx Detection Parameter)

The first detection device sets the SOx decomposition period to be equal to or greater than a predetermined time by performing the SOx detection voltage control. The first detection device acquires a parameter (a SOx detection parameter Ismn) appropriately (accurately) indicating a "reoxidation current change" from an output current and determines whether the SOx concentration in the exhaust gas is equal to or higher than a predetermined value based on the acquired parameter.

More specifically, the first detection device acquires a minimum value of an output current Im (hereinafter referred to as a "minimum current Ismn" or a "minimum value Ismn") when the application voltage Vm is in a "range (a detection voltage range) which is equal to or lower than a current acquisition start voltage (a third voltage) Vsem and equal to or higher than a fourth voltage V4 higher than the first voltage V1" in the third application voltage control (the step-down sweep) as the "parameter indicating the reoxidation current change."

The current acquisition start voltage Vsem is selected in a range which is higher than a lower limit voltage (the first voltage V1) of the step-down sweep (the third application voltage control) in which the reoxidation current change appears in the output current Im and equal to or lower than the SOx decomposition start voltage (0.6 V). In this example, the current acquisition start voltage Vsem is set to 0.6 V. The current acquisition start voltage Vsem may change depending on at least one of the application voltage range and the cycle of the application voltage sweep (that is, the sweeping rate of the application voltage sweep). The first detection device detects the SOx concentration based on the SOx detection parameter (the minimum current Ismn).

SOx Concentration Detecting Method

The first detection device performs detection of the SOx concentration using the above-mentioned SOx concentration detection principle as follows.

The first detection device performs application voltage control for detection of SOx (SOx detection voltage control). Specifically, the first detection device performs the SOx detection voltage control including first application voltage control (a step-up sweep), second application voltage control (voltage maintaining control), and third application voltage control (a step-down sweep). The third application voltage control is performed at the above-mentioned "predetermined sweeping rate."

The first detection device acquires an output current Im when the application voltage Vm is in a detection voltage range (which is equal to or lower than the current acquisition start voltage Vsem and equal to or higher than the fourth voltage V4 higher than the first voltage V1) during the third application voltage control (during the step-down sweep) and acquires a minimum value thereof as the minimum current Ismn. The minimum current Ismn is the parameter indicating the SOx concentration in the exhaust gas ("SOx detection parameter"). The SOx detection parameter is acquired from the output current Im when the SOx detection voltage control in which the SOx decomposition period is set to be equal to or greater than a predetermined time is performed. Accordingly, the difference depending on the SOx concentration (the difference between when the SOx concentration is equal to or higher than a predetermined value and the SOx concentration is lower than the predetermined value) which is required for detection of the SOx concentration appears distinctly in the SOx detection parameter.

The first detection device detects the SOx concentration based on the SOx detection parameter (the minimum current Ismn).

Specifically, when the SOx detection voltage control is performed, the first detection device applies the application voltage Vm which is controlled as illustrated in FIG. 8B across the first electrode 41a and the second electrode 41b. When the third application voltage control (the step-down sweep) is performed, the first detection device performs an application voltage sweep (the step-down sweep) at the above-mentioned "predetermined sweeping rate" at which a significant current change occurs in detection of the SOx concentration.

As described above, when the step-up sweep and the step-down sweep are performed and SOx is contained in the exhaust gas, S (sulfur) produced by decomposition of SOx is adsorbed on the first electrode 41a mainly in a period in which the step-up sweep is performed. Mainly In the period in which the step-down sweep is performed, S adsorbed on the first electrode 41a is re-oxidized.

The first detection device detects the SOx concentration by detecting the reoxidation current change using the SOx detection parameter (=the minimum current Ismn). That is, the first detection device performs the application voltage sweep and acquires a minimum value (the minimum current Ismn) when the application voltage Vm is in the above-mentioned detection voltage range (the range which is equal to or higher than the fourth voltage V4 and equal to or lower than Vsem in FIG. 8B) during the step-down sweep from the output current Im indicated by a line g1 in FIG. 8B.

When SOx is contained in the exhaust gas (the line g1), the degree of reoxidation current change is greater than that when SOx is not contained in the exhaust gas (the line g2). That is, in the detection voltage range, the output current Im, which is indicated by the line g1, when SOx is contained in the exhaust gas is smaller than the output current Im, which is indicated by the line g2, when SOx is not contained in the exhaust gas. The minimum current Ismn when SOx is contained in the exhaust gas is smaller than the minimum current Ir when SOx is not contained in the exhaust gas. As the SOx concentration in the exhaust gas increases, the reoxidation current change becomes more remarkable and thus the minimum current Ismn decreases. Accordingly, the first detection device acquires the minimum current Ismn as the SOx detection parameter indicating the SOx concentration.

According to the first detection device, the value of the output current Im (the minimum current Ismn) accurately indicating a degree of reoxidation current change which is required for detection of the SOx concentration is acquired as the SOx detection parameter in this way. Accordingly, even when an actual voltage at which the minimum current smn appears changes depending on all the conditions (for example, the air-fuel ratio A/F of the engine, the application voltage range, the sweeping rate, the sensor element temperature of the gas sensor 30, and an aging characteristic change of the gas sensor 30), it is possible to satisfactorily acquire the minimum current Ismn. Accordingly, the first detection device can more accurately detect the SOx concentration.

The minimum current Ismn is acquired from the output current Im when the SOx detection voltage control in which the SOx decomposition period is set to be equal to or greater than a predetermined time is performed. Accordingly, the difference depending on the SOx concentration required for detection of the SOx concentration appears distinctly in the minimum current Ismn. As a result, it is possible to more accurately detect the SOx concentration. Particularly, even when the SOx concentration in the exhaust gas is low and thus the difference depending on the SOx concentration does not appear distinctly in the output current Im, the difference depending on the SOx concentration required for detection of the SOx concentration appears and thus it is possible to accurately detect the SOx concentration.

Specific Operation

Figure 10:
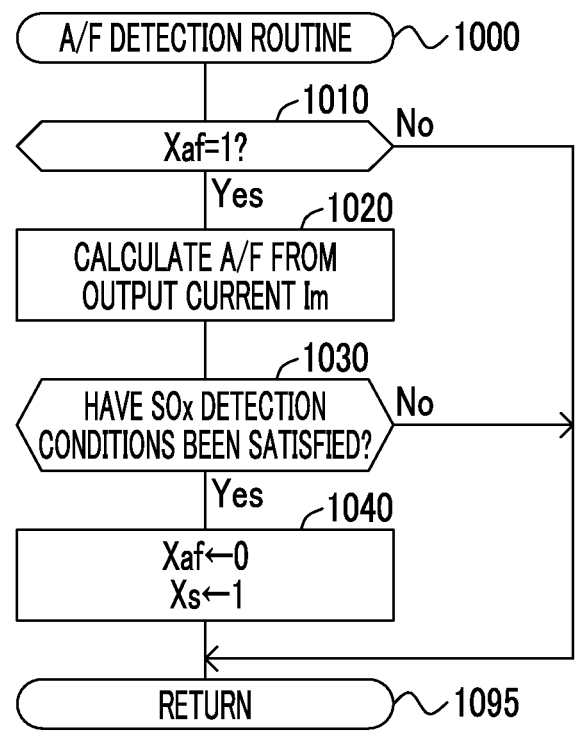
FIG. 10 is a flowchart illustrating an A/F detection routine which is performed by the CPU of the ECU in the gas detection device according to the first embodiment of the disclosure.
Figure 11:
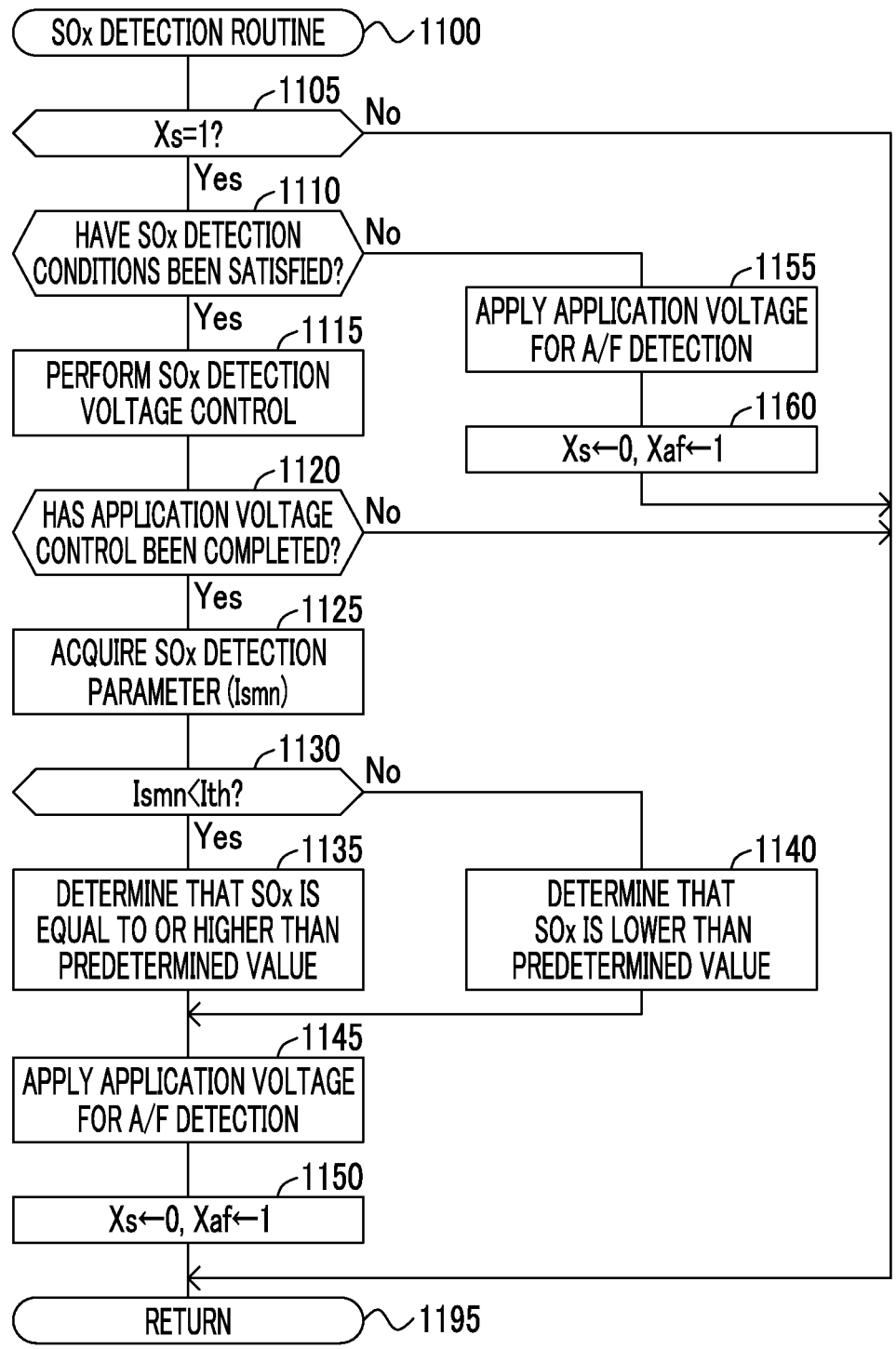
FIG. 11 is a flowchart illustrating a SOx detection routine which is performed by the CPU of the ECU in the gas detection device according to the first embodiment of the disclosure.

A specific operation of the first detection device will be described below. The CPU of the ECU 20 (hereinafter simply referred to as a "CPU") performs a sensor activation determination routine, an A/F detection routine, and a SOx detection routine which are illustrated in the flowcharts of FIGS. 9 to 11 using the gas sensor 30 at predetermined time intervals.

A "value of an A/F detection request flag Xaf and a value of a SOx detection request flag Xs" which are used in the routines are set to "0" in an initial routine which is performed by the CPU when an ignition key switch (not illustrated) which is mounted in the vehicle is changed from an OFF position to an ON position.

Figure 9:
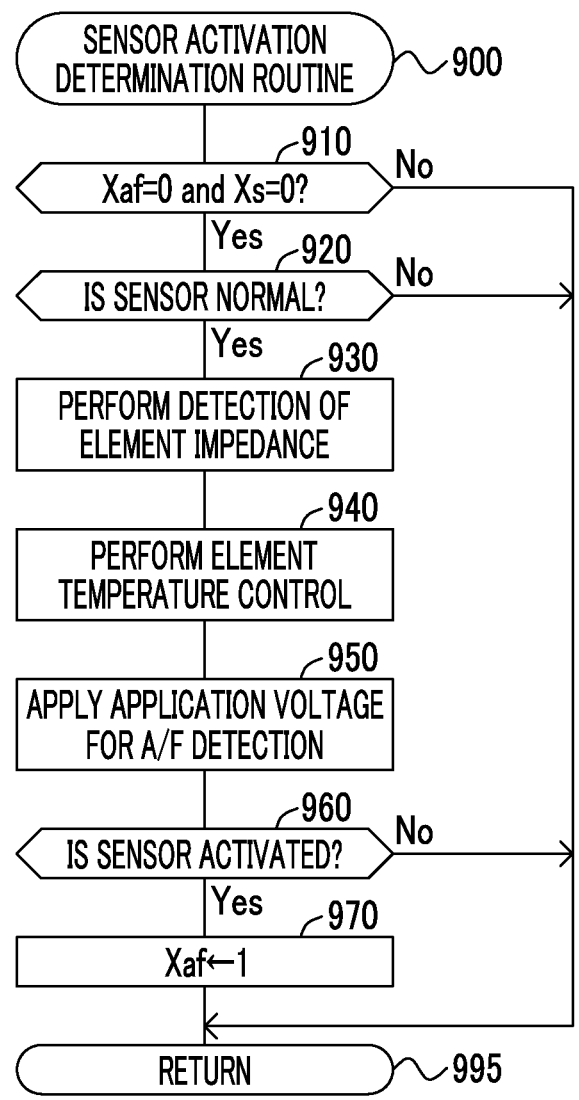
FIG. 9 is a flowchart illustrating a sensor activation determination routine which is performed by a CPU of an ECU in the gas detection device according to the first embodiment of the disclosure.

At a predetermined time, the CPU starts the routine from Step 900 in the sensor activation determination routine illustrated in FIG. 9 and determines whether both the value of the A/F detection request flag Xaf and the value of the SOx detection request flag Xs are "0" in Step S910.

Immediately after the ignition key switch is changed to the ON position (immediately after the internal combustion engine 10 is started), both the value of the A/F detection request flag Xaf and the value of the SOx detection request flag Xs are "0." In this case, the CPU determines "YES" in Step 910 and determines whether the gas sensor 30 is normal using a well-known method in Step 920. For example, when the operation state of the internal combustion engine 10 is changed from a fuel injection state to a fuel-cut state during the A/F detection in the previous operation of the internal combustion engine 10 and the output current Is does not change, the CPU determines that the gas sensor 30 is abnormal and stores the purport in the backup RAM which can maintain storage details even when the ignition key switch is turned off. Then, in Step 920 of the routine, the CPU determines whether the gas sensor 30 is normal based on the storage details of the backup RAM.

When the gas sensor 30 is normal, the CPU determines "YES" in Step 920 and detects element impedance for element temperature control in Step 930 (internal resistance of the solid electrolyte 41s) based on the output current Im when a voltage (for example, a high-frequency voltage) is applied across the first electrode 41a and the second electrode 41b in Step 930 (for example, see Japanese Unexamined Patent Application Publication No. H10-232220 (JP H10-232220 A) and Japanese Unexamined Patent Application Publication No. 2002-232220 (JP 2002-71633 A)).

Thereafter, the CPU sequentially performs the processes of Step 940 and Step 950 and then perform the process of Step 960. The CPU performs heater power supply control by target impedance feedback (Step 940). That is, supply of power to the heater 71 is controlled such that the element impedance acquired in Step 930 as temperature information matches preset target impedance (for example, see JP 2002-71633 A and Japanese Unexamined Patent Application Publication No. 2009-53108 (JP 2009-53108 A)). The CPU applies the application voltage Vm (specifically, 0.4 V) for detection of an oxygen concentration (that is, for A/F detection) across the first electrode 41a and the second electrode 41b (Step 950). That is, the CPU sets the application voltage Vm to the oxygen concentration detection application voltage Vaf.

In Step 960, the CPU determines whether the gas sensor 30 is activated (in a sensor-activated state). Specifically, the CPU determines whether the temperature of the solid electrolyte 41s which is estimated based on the element impedance acquired in Step 930 is equal to or higher than an activation temperature threshold value. When the gas sensor 30 is not in the sensor-activated state, the CPU determines "NO" in Step 960 and temporarily ends this routine in Step 995.

On the other hand, when the gas sensor 30 is in the sensor-activated state, the CPU determines "YES" in Step 960 and sets the value of the A/F detection request flag Xaf to "1" in Step 970. Thereafter, the CPU temporarily ends this routine in Step 995.

When one of the value of the A/F detection request flag Xaf and the value of the SOx detection request flag Xs is not "0" at a time point at which the CPU performs the process of Step 910, the CPU determines "NO" in Step 910 and temporarily ends this routine in Step 995.

The A/F detection routine will be described below with reference to FIG. 10. At a predetermined time, the CPU starts this routine from Step 1000 in FIG. 10 and determines whether the value of the A/F detection request flag Xaf is "1" in Step 1010.

The A/F detection routine functions substantially when the SOx detection request flag Xs is in an OFF state (Xs=0) after a time point at which the gas sensor 30 enters in the sensor-activated state and the value of the A/F detection request flag Xaf is set to "1." Accordingly, when the value of the A/F detection request flag Xaf is not "1" (that is, when the value of the A/F detection request flag Xaf is "0"), the CPU determines "NO" in Step 1010 and temporarily ends this routine in Step 1095.

On the other hand, when the value of the A/F detection request flag Xaf is set to "1" through the process of Step 970 in FIG. 9 or when the value of the A/F detection request flag Xaf is set to "1" through the processes of Steps 1150 and 1160 in FIG. 11 which will be described later, the CPU determines "YES" in Step 1010 and calculates the air-fuel ratio A/F of the engine by detecting an oxygen concentration based on the output current Im acquired from the gas sensor 30 and applying the detected oxygen concentration to a predetermined lookup table (also referred to as a "map") in Step 1020. Thereafter, in Step 1030, the CPU determines whether all conditions of the following SOx detection conditions are satisfied based on information acquired from various sensors (such as the NE sensor 21 and the coolant temperature sensor 22). When all of the following conditions are satisfied, the SOx detection conditions are satisfied.

SOx Detection Conditions

The internal combustion engine 10 is in a warmed-up state (that is, the coolant temperature THW is equal to or higher than a warm-up coolant temperature THWth.).

The gas sensor 30 is in the sensor-activated state.

The internal combustion engine is not in a fuel-cut state.

The air-fuel ratio A/F of the engine is stabilized.

That is, the operation state of the internal combustion engine 10 is an idling state or the driving state of the vehicle is a normal traveling state. Whether the operation state of the internal combustion engine 10 is an idling state is determined by determining whether a "state in which the accelerator pedal depression amount AP is "0" and the engine rotation speed NE is equal to or lower than a predetermined rotation speed" is continuously maintained over a predetermined idling time. Whether the driving state of the vehicle is a normal traveling state is determined by determining whether a "state in which a change per unit time of the accelerator pedal depression amount AP is equal to or less than a threshold operation change and a change per unit time of a vehicle speed detected by a vehicle speed sensor which is not illustrated is equal to or lower than a threshold vehicle speed change" is continuously maintained over a predetermined normal traveling threshold time.

Before the ignition key switch is changed to the OFF position after the ignition key switch is changed from the OFF position to the ON position (that is, after the internal combustion engine 10 is currently started), the SOx concentration is not performed at all.

When the SOx detection conditions are satisfied, the CPU determines "YES" in Step 1030, and sets the value of the A/F detection request flag Xaf to "0" and sets the value of the SOx detection request flag Xs to "1" in Step 1040.

On the other hand, when at least one of the conditions constituting the SOx detection conditions is not satisfied, the CPU determines "NO" in Step 1030 and temporarily ends this routine in Step 1095.

The SOc detection routine will be described below with reference to FIG. 11. At a predetermined time, the CPU starts the routine from Step 1100 in the SOx detection routine illustrated in FIG. 11 and determines whether the value of the SOx detection request flag Xs is "1" in Step S1105.

The SOx detection routine functions substantially when the SOx detection conditions are satisfied (that is, when the SOx detection request flag Xs is turned on (Sx=1)). Accordingly, when the value of the SOx detection request flag Xs is not "1" (that is, the value of the SOx detection request flag Xs is "0"), the CPU determines "NO" in Step 1105 and temporarily ends this routine in Step 1195.

On the other hand, when the value of the SOx detection request flag Xs is set to "1" through the process of Step 1040 in FIG. 10, the CPU determines "YES" in Step 1105 and determines whether all the conditions constituting the SOx detection conditions are satisfied in Step 1110.

When the SOx detection conditions are satisfied, the CPU determines "YES" in Step 1110 and performs the SOx detection voltage control in Step 1115. Specifically, the CPU performs the first application voltage control, the second application voltage control, and the third application voltage control which are described below in this order as the SOx detection voltage control.

First Application Voltage Control

A step-up sweep (1 second) of slowly stepping up the application voltage Vm from a first voltage V1 (0.4 V) to a second voltage V2 (0.8 V)

Second Application Voltage Control

Application voltage control (10 seconds) of maintaining the application voltage Vm at the same voltage as a voltage (0.8 V) at a time point at which the first application voltage control ends over a predetermined voltage maintaining time Third Application Voltage Control A step-down sweep (1 second) of slowly stepping down the application voltage Vm from 0.8 V to the first voltage V1 (0.4 V)

When the SOx detection voltage control is already performed at a time point at which the process of Step S1115 is performed, the CPU continues to perform the SOx detection voltage control.

Thereafter, the CPU determines whether the SOx detection voltage control is completed in Step 1120.

When the SOx detection voltage control is not completed, the CPU determines "NO" in Step 1120 and temporarily ends the routine in Step 1195.

When the SOx detection voltage control is completed, the CPU determines "YES" in Step 1120 and acquires the SOx detection parameter (the minimum current Ismn) from the output current Im acquired by performing the SOx detection voltage control in Step S1125.

Thereafter, in Step 1130, the CPU determines whether the minimum current Ismn is less than a threshold value (a threshold minimum current) Ith. The threshold minimum current Ith is a value suitable for determining whether the SOx concentration in the exhaust gas is equal to or higher than a predetermined value (performing SOx concentration determination) and is specified in advance by experiment or the like. That is, the threshold minimum current Ith is set to a minimum value of the output current Im in the detection voltage range during the step-down sweep when sulfur (S) with a concentration corresponding to a predetermined value (for example, an upper limit concentration of an allowable range) is mixed into fuel and the application voltage control is performed under the same conditions as described above (the same conditions as when the SOx concentration in the exhaust gas is actually detected). In this case, the same conditions are the same in a voltage waveform of the application voltage control, an application voltage range of the application voltage control, a sweeping rate and a detection voltage range of the application voltage control, and the like.

The CPU may change the value of the threshold minimum current Ith depending on the A/F acquired in Step 1020 in FIG. 9. Specifically, the CPU may change the threshold minimum current Ith such that the threshold minimum current Ith becomes larger as the air-fuel ratio A/F acquired through the process of Step 1020 becomes higher. The reason is as follows.

As the air-fuel ratio A/F of the engine becomes higher, more oxide ions migrate from the first electrode 41a to the second electrode 41b due to reductive decomposition of oxygen (oxygen molecules ($O_2$)) in the exhaust gas and thus the output current Im increases. In some embodiments, the threshold minimum current Ith may be changed in consideration of the increase of the output current Im. Accordingly, it is possible to "more accurately" determine whether SOx with a "predetermined concentration" is contained in the exhaust gas regardless of the air-fuel ratio A/F of the engine. In this case, the CPU may determine the threshold minimum current Ith for each A/F by applying the air-fuel ratio A/F acquired through the process of Step 1020 to a predetermined lookup table.

In some embodiments, the CPU sets the value of the threshold minimum current Ith to change depending on the SOx decomposition period of the SOx detection voltage control which is performed in Step 1115. Even when the SOx concentration in the exhaust gas is constant, a degree of decrease of the output current Im increases as the SOx decomposition period becomes longer and the threshold minimum current Ith may be changed in consideration of an increase in the degree of decrease of the output current Im. In some embodiments, the value of the threshold minimum current Ith used for the SOx concentration determination (determination of whether the SOx concentration in the exhaust gas is equal to or higher than a predetermined value) becomes less as the SOx decomposition period becomes longer. The CPU may determine the threshold minimum current Ith depending on the SOx decomposition period by applying the SOx decomposition period acquired through the process of Step 1115 to a predetermined lookup table.

When the minimum current Ismn is less than the threshold minimum current Ith, the reoxidation current change is large. Accordingly, the CPU determines "YES" in Step 1130 and determines that the SOx concentration in the exhaust gas is equal to or higher than a predetermined value in Step 1135. At this time, the CPU may store the purport indicating that the SOx concentration in the exhaust gas is equal to or higher than the predetermined value (or the purport indicating that S exceeding an allowable value is mixed into fuel)

in the backup RAM or may turn on a predetermined warning lamp. Thereafter, the CPU performs the process of Step 1145.

On the other hand, when the minimum current Ismn is equal to or greater than the threshold minimum current Ith, the CPU determines "NO" in Step 1130 and determines that the SOx concentration in the exhaust gas is less than the predetermined value in Step 1140. At this time, the CPU may store the purport indicating that the SOx concentration in the exhaust gas is less than the predetermined value (or the purport indicating that S exceeding an allowable value is not mixed into fuel) in the backup RAM or may turn off a predetermined warning lamp. Thereafter, the CPU performs the process of Step 1145.

In Step 1145, the CPU applies the oxygen concentration detection application voltage Vaf (specifically, 0.4 V) across the first electrode 41a and the second electrode 41b. Thereafter, in Step 1150, the CPU sets the value of the SOx detection request flag Xs to "0" and sets the value of the A/F detection request flag Xaf to "1." Thereafter, the CPU temporarily ends this routine in Step 1195.

When the SOx detection conditions are not satisfied at a time point at which the process of Step 1110 is performed, the CPU determines "NO" in Step 1110 and applies the oxygen concentration detection application voltage Vaf (specifically, 0.4 V) across the first electrode 41a and the second electrode 41b in Step 1155. Thereafter, in Step 1160, the CPU sets the value of the SOx detection request flag Xs to "0" and sets the value of the A/F detection request flag Xaf to "1." Thereafter, the CPU temporarily ends this routine in Step 1195.

As described above, the first detection device performs the SOx detection voltage control in which the SOx decomposition period is set to be longer. Accordingly, the difference depending on the SOx concentration (the difference between when the SOx concentration is equal to or higher than a predetermined value and the SOx concentration is lower than the predetermined value) appears distinctly in the SOx detection parameter (the minimum current Ismn) acquired from the output current Im when the SOx detection voltage control is performed. As a result, it is possible to accurately detect the SOx concentration. Particularly, even when the determination value of the criterion for the SOx concentration determination is low, the difference depending on the SOx concentration (the difference between when the SOx concentration is equal to or higher than a predetermined value and the SOx concentration is lower than the predetermined value) appears distinctly in the SOx detection parameter (the minimum current Ismn) and thus it is possible to accurately detect the SOx concentration even when the SOx concentration in the exhaust gas is low.

Second Embodiment

A gas detection device according to a second embodiment of the disclosure (hereinafter also referred to as a "second detection device") will be described below. The second detection device is different from the first detection device in only the following points. The first detection device determines whether the SOx concentration in the exhaust gas is equal to or higher than the predetermined value based on the SOx detection parameter (the minimum current Ismn) which is acquired by performing the SOx detection voltage control. On the other hand, the second detection device determines whether the SOx concentration in the exhaust gas is equal to or higher than a first predetermined value based on a SOx detection parameter (the minimum current Ismn) which is acquired by performing a first SOx detection voltage control. When it is determined that the SOx concentration in the exhaust gas is lower than the first predetermined value, a second SOx detection voltage control is performed such that the SOx decomposition period is longer than the SOx decomposition period in the previous SOx detection voltage control. It is determined whether the SOx concentration in the exhaust gas is equal to or higher than a second predetermined value which is set to be lower than the first predetermined value based on the SOx detection parameter (the minimum current Ismn) which is acquired by performing the second SOx detection voltage control. Hereinafter, this difference will be mainly described.

Specific Operation

A specific operation of the second detection device will be described below. The CPU of the ECU 20 performs the same sensor activation determination routine as the routine illustrated in FIG. 9, the same A/F detection routine as the routine illustrated in FIG. 10, and SOx detection routine 1 illustrated in FIG. 12, and SOx detection routine 2 illustrated in FIG. 13 at predetermined time intervals.

A sensor activation determination routine and an A/F detection routine are the same as performed by the first detection device and have been described above already. Accordingly, description thereof will not be repeated.

Figure 12:
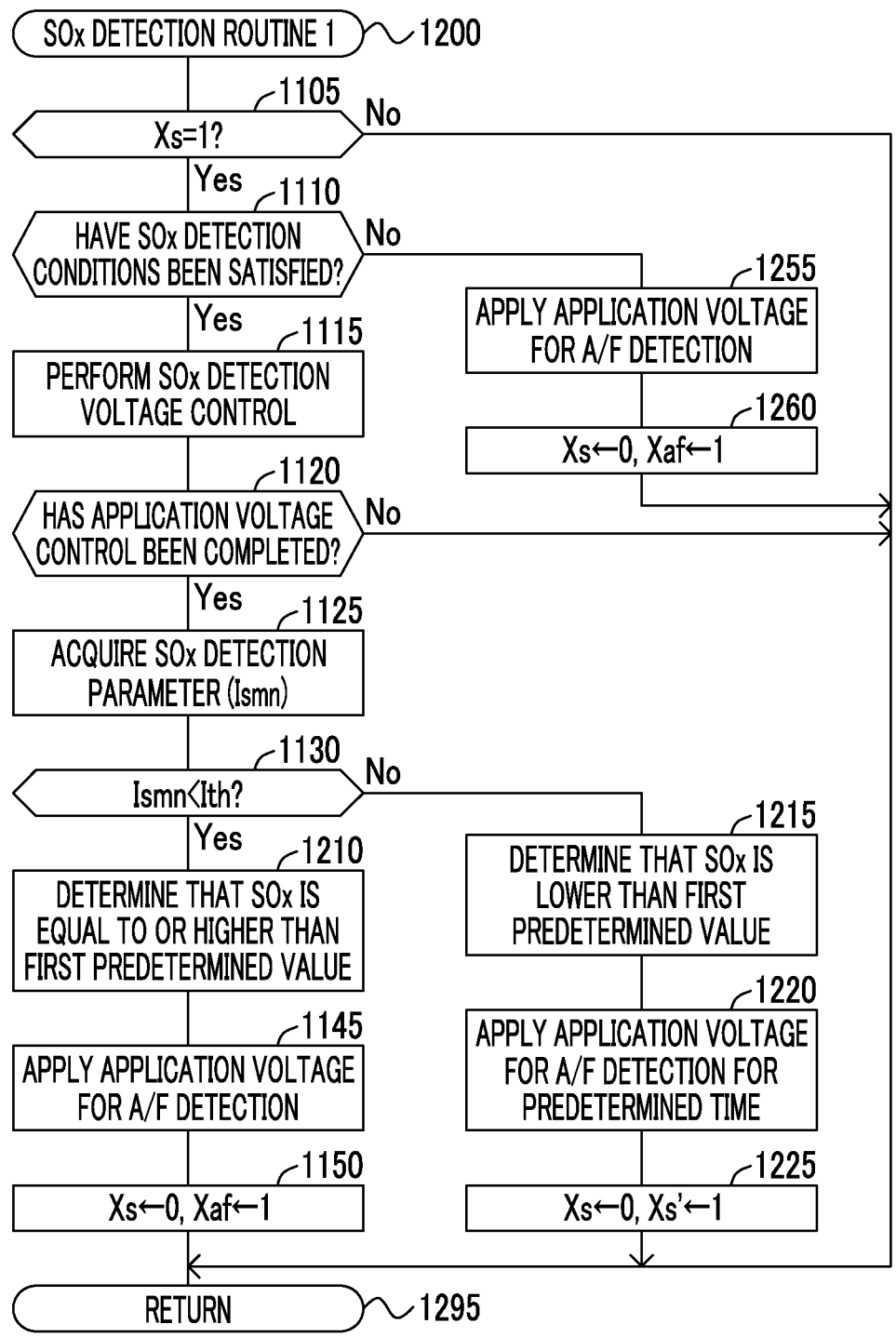
FIG. 12 is a flowchart illustrating SOx detection routine 1 which is performed by a CPU of an ECU in a gas detection device according to a second embodiment of the disclosure.

SOx detection routine 1 will be described below with reference to FIG. 12. The routine illustrated in FIG. 12 is different from the routine illustrated in FIG. 11 in only the following points. Steps 1135 and 1140 in FIG. 11 are replaced with Steps 1210 and 1215. Steps 1220 and 1225 are added between Steps 1140 and 1195 in FIG. 11. Hereinafter, these differences will be mainly described.

When the minimum current Ismn is less than the threshold minimum current Ith, the reoxidation current change is large, and thus the CPU determines "YES" in Step 1130 and determines that the SOx concentration in the exhaust gas is equal to or higher than the first predetermined value in Step 1210 (Step 1210).

When the minimum current Ismn is equal to or greater than the threshold minimum current Ith, the CPU determines "NO" in Step 1130 and determines that the SOx concentration in the exhaust gas is less than the first predetermined value in Step 1215 (Step 1215). Thereafter, in Step 1220, the CPU applies the oxygen concentration detection application voltage Vaf (specifically, 0.4 V) across the first electrode 41a and the second electrode 41b for a predetermined time (Step 1220). Thereafter, in Step 1225, the CPU sets the value of the SOx detection request flag Xs to "0" and sets the value of a SOx redetection request flag Xs' to "1." Thereafter, the CPU temporarily ends this routine in Step 1295.

Figure 13:
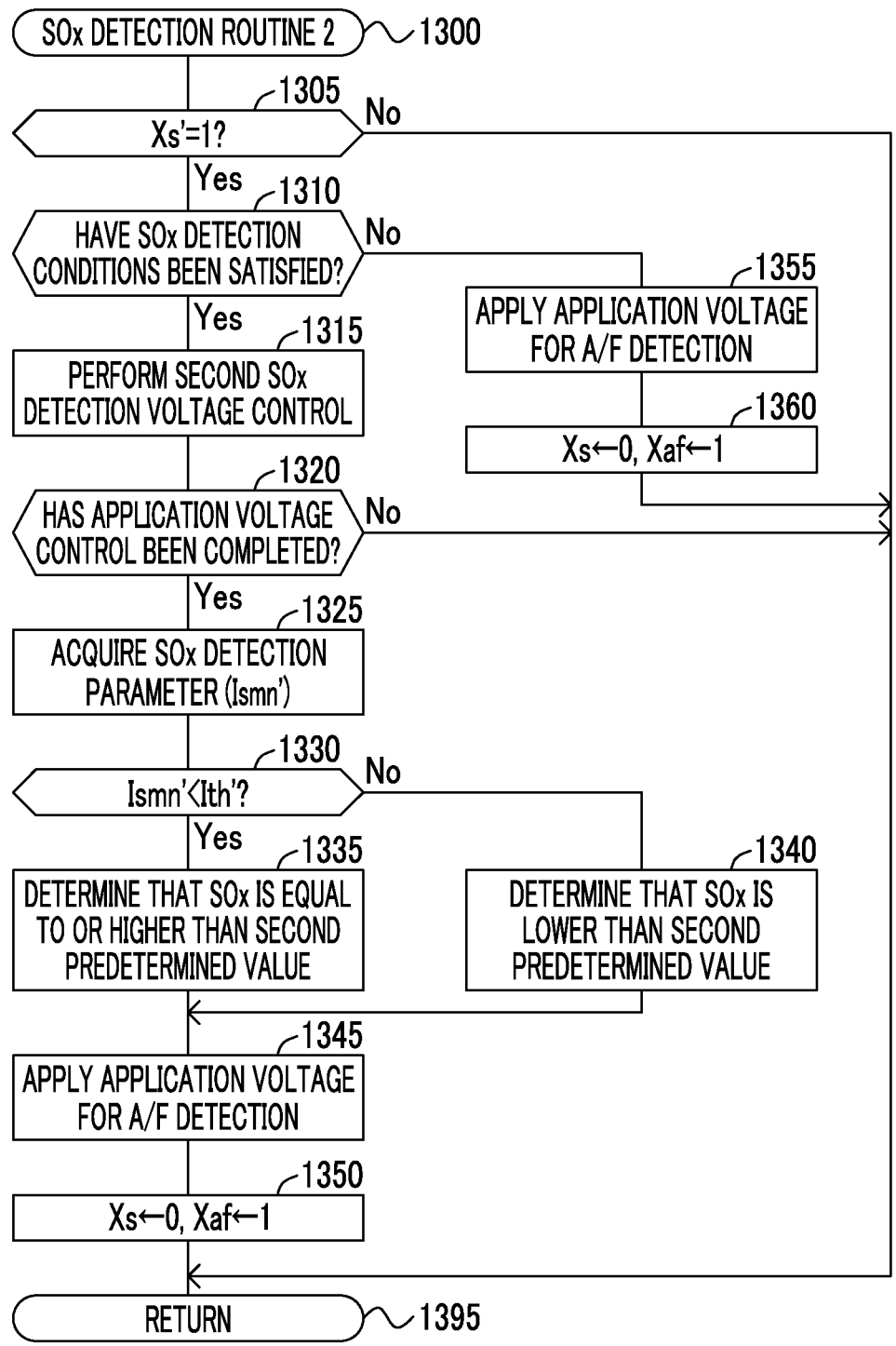
FIG. 13 is a flowchart illustrating SOx detection routine 2 which is performed by the CPU of the ECU in the gas detection device according to the second embodiment of the disclosure.

SOx detection routine 2 will be described below with reference to FIG. 13. At a predetermined time, the CPU starts this routine from Step 1300 in SOx detection routine 2 illustrated in FIG. 13 and determines whether the value of the SOx redetection request flag Xs' are "0" in Step S1305.

SOx detection routine 2 functions substantially when it is determined in SOx detection routine 1 that the SOx concentration in the exhaust gas is lower than the first predetermined value. Accordingly, when the value of the SOx redetection request flag Xs' is not "1" (that is, when the value of the SOx redetection request flag Xs' is "0"), the CPU determines "YES" in Step 1305 and determines whether all of the conditions constituting the SOx detection conditions are satisfied in Step 1310.

When the SOx detection conditions are satisfied, the CPU determines "YES" in Step 1310 and performs the second SOx detection voltage control in Step 1315. In the second SOx detection voltage control, the voltage maintaining time of the second application voltage control is set to be longer than that in the first SOx detection voltage control such that the SOx decomposition period is longer than that in the first SOx detection voltage control. The second SOx detection voltage control is different from the first SOx detection voltage control, only in that the time of the second application voltage control is set to be longer, but the sweeping ranges of the first application voltage control and the third application voltage control are the same as in the first SOx detection voltage control. The second application voltage control of the second SOx detection voltage control may be referred to as "corrected second application voltage control" for the purpose of convenience.

Specifically, the CPU performs first application voltage control, second application voltage control, and third application voltage control as the second SOx detection voltage control as described below.

First Application Voltage Control

A step-up sweep (1 second) of slowly stepping up the application voltage Vm from the first voltage V1 (0.4 V) to the second voltage V2 (0.8 V)

Second Application Voltage Control

Application voltage control (30 seconds) of maintaining the application voltage Vm at the same voltage as a voltage (0.8 V) at a time point at which the first application voltage control ends over a predetermined voltage maintaining time Third Application Voltage Control A step-down sweep (1 second) of slowly stepping down the application voltage Vm from 0.8 V to the first voltage V1 (0.4 V)

When the second SOx detection voltage control is already performed at a time point in which the process of Step S1315 is performed, the CPU continues to perform the SOx detection voltage control.

Thereafter, the CPU determines whether the second SOx detection voltage control is completed in Step 1320.

When the second SOx detection voltage control is not completed, the CPU determines "NO" in Step 1320 and temporarily ends the routine in Step 1395.

When the second SOx detection voltage control is completed, the CPU determines "YES" in Step 1320 and acquires the SOx detection parameter (the minimum current Ismn') from the output current Im acquired by performing the second SOx detection voltage control in Step S1325.

Thereafter, in Step 1330, the CPU determines whether the minimum current Ismn' is less than a threshold value (a threshold minimum current) Ith'. The threshold minimum current Ith' is a value suitable for determining whether the SOx concentration in the exhaust gas is equal to or higher than a second predetermined value set to a value lower than the first predetermined value (performing SOx concentration determination) and is specified in advance by experiment or the like. Similarly to the threshold minimum current Ith which is used in Step 1115, the CPU may set the value of the threshold minimum current Ith' to change depending on the A/F or may set the value of the threshold minimum current Ith' to change depending on the SOx decomposition period of the second SOx detection voltage control.

When the minimum current Ismn' is less than the threshold minimum current Ith', the reoxidation current change is large. Accordingly, the CPU determines "YES" in Step 1330 and determines that the SOx concentration in the exhaust gas is equal to or higher than a second predetermined value in Step 1335. At this time, the CPU may store the purport indicating that the SOx concentration in the exhaust gas is equal to or higher than the second predetermined value in the backup RAM or may turn on a predetermined warning lamp. Thereafter, the CPU performs the process of Step 1345.

On the other hand, when the minimum current Ismn' is equal to or greater than the threshold minimum current Ith', the CPU determines "NO" in Step 1330 and determines that the SOx concentration in the exhaust gas is less than a second predetermined value in Step 1340. At this time, the CPU may store the purport indicating that the SOx concentration in the exhaust gas is less than the second predetermined value (or the purport indicating that S exceeding the allowable value is not mixed into fuel) in the backup RAM or may turn off a predetermined warning lamp. Thereafter, the CPU performs the process of Step 1345.

In Step 1345, the CPU applies the oxygen concentration detection application voltage Vaf (specifically, 0.4 V) across the first electrode 41a and the second electrode 41b. Thereafter, in Step 1350, the CPU sets the value of the SOx redetection request flag Xs' to "0" and sets the value of the A/F detection request flag Xaf to "1." Thereafter, the CPU temporarily ends this routine in Step 1395.

When the SOx detection conditions are not satisfied at a time point at which the process of Step 1310 is performed, the CPU determines "NO" in Step 1310 and applies the oxygen concentration detection application voltage Vaf (specifically, 0.4 V) across the first electrode 41a and the second electrode 41b in Step 1355. Thereafter, in step 1360, the CPU sets the value of the SOx redetection request flag Xs' to "0" and sets the value of the A/F detection request flag Xaf to "1." Thereafter, the CPU temporarily ends this routine in Step 1395.

As described above, the second detection device achieves the same advantages as the first detection device. When it is determined whether the SOx concentration in the exhaust gas is equal to or higher than a concentration (the second predetermined value) lower than that in the first SOx concentration determination, the second detection device sets the SOx decomposition period of the second SOx detection voltage control to be longer than that in the first SOx detection voltage control. Accordingly, even when the SOx concentration in the exhaust gas is low (the SOx concentration is lower than the first predetermined value), the difference depending on the SOx concentration (the difference 16 between when the SOx concentration is equal to or higher than a second predetermined value and the SOx concentration is lower than the second predetermined value) appears distinctly in the SOx detection parameter and thus it is possible to accurately determine whether the SOx concentration in the exhaust gas is equal to or higher than the second predetermined value (determine whether the SOx concentration in the exhaust gas is equal to or lower than the SOx concentration lower than that in the first SOx concentration determination).

Third Embodiment

Figure 14:
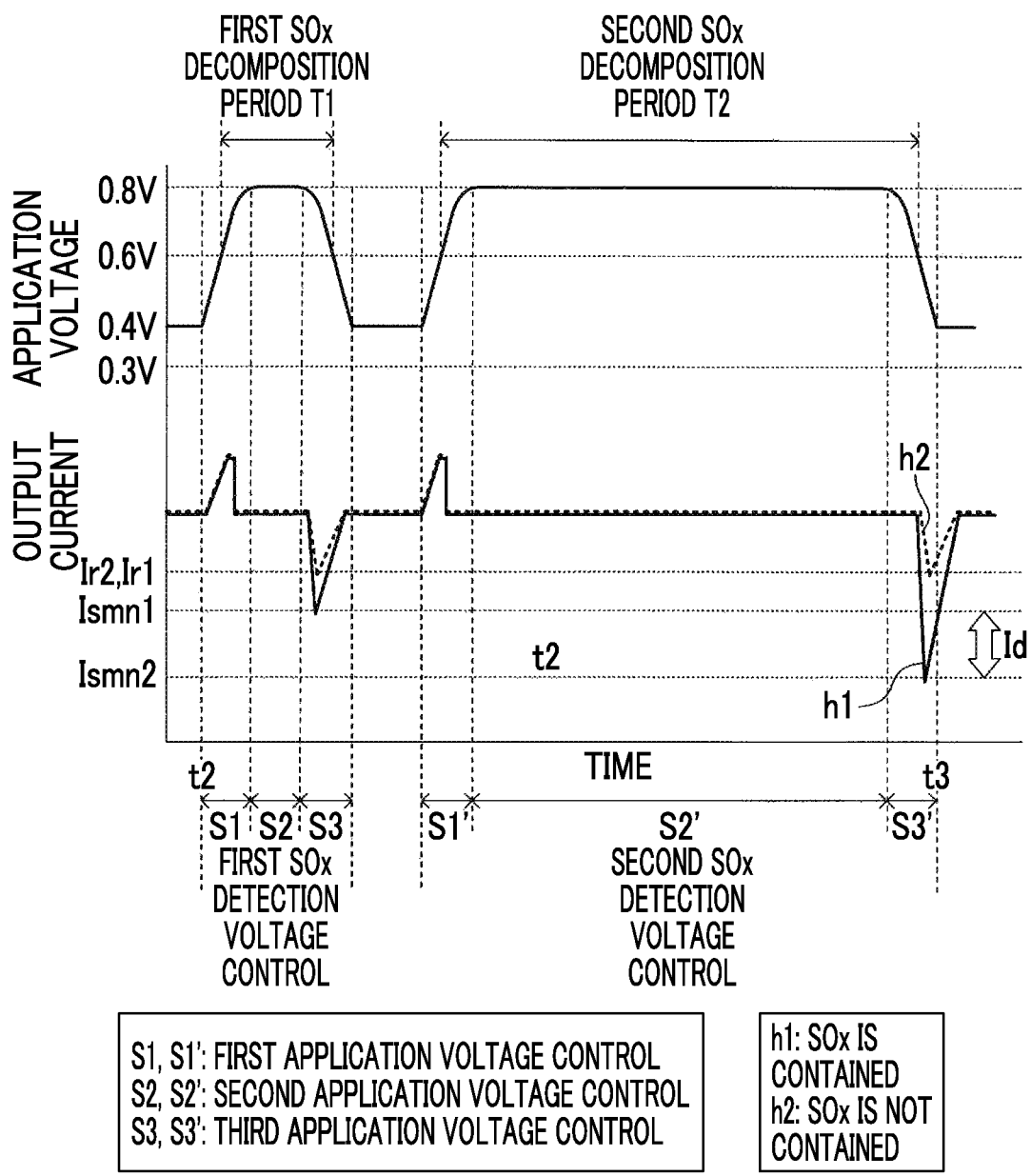
FIG. 14 is a graph illustrating a relationship between an elapsed time and each of an application voltage and an output current.

A gas detection device according to a third embodiment of the disclosure (hereinafter also referred to as a "third detection device") will be described below. The third detection device is different from the first detection device in only the following points. As illustrated in FIG. 14, the third detection device performs first SOx detection voltage control in which the SOx decomposition period is set to a first SOx decomposition period T1 and second SOx detection voltage control in which the SOx decomposition period is set to a second SOx decomposition period T2 longer than the first SOx decomposition period. The third detection device acquires a first SOx detection parameter (a minimum current Ismn1) from the output current Im acquired when the first SOx detection voltage control is performed, and acquires a second SOx detection parameter (a minimum current Ismn2) from the output current Im acquired when the second SOx detection voltage control is performed. The third detection device calculates an absolute value of a difference (Ismn1−Ismn2) (a difference magnitude) Id between the first SOx detection parameter (the minimum current Ismn1) and the second SOx detection parameter (the minimum current Ismn2). According to comparison of the difference magnitude Id when SOx is contained in the exhaust gas illustrated in FIG. 14 and the difference magnitude (Ir1−Ir2) when SOx is not contained in the exhaust gas and comparison of the difference magnitude Id illustrated in FIG. 7A and the difference magnitude Id illustrated in FIG. 7B, the difference magnitude Id increases as the SOx concentration in the exhaust gas becomes higher. The third detection device determines whether the SOx concentration in the exhaust gas is equal to or higher than a predetermined value based on the difference magnitude Id. Hereinafter, this difference will be mainly described.

Specific Operation

A specific operation of the third detection device will be described below. The CPU of the ECU 20 performs the same sensor activation determination routine as the routine illustrated in FIG. 9, the same A/F detection routine as the routine illustrated in FIG. 10, SOx detection routine 1 illustrated in FIG. 15, and SOx detection routine 2 illustrated in FIG. 16 at predetermined time intervals.

The sensor activation determination routine and the A/F detection routine are the same as the routines performed by the first detection device and have been described above. Accordingly, description thereof will not be repeated.

SOx detection routine 1 will be described below with reference to FIG. 15. At a predetermined time, the CPU starts this routine from Step 1500 in SOx detection routine 1 illustrated in FIG. 15 and determines whether the value of the first SOx detection request flag Xs1 is "1" in Step S1505.

SOx detection routine 1 functions substantially when the SOx detection conditions are satisfied (that is, when the first SOx detection request flag Xs1 is in the ON state (Xs1=1)). Accordingly, when the value of the first SOx detection request flag Xs1 is not "1" (that is, when the value of the first SOx detection request flag Xs1 is "0"), the CPU determines "NO" in Step 1505 and temporarily ends this routine in Step 1595.

On the other hand, when the value of the first SOx detection request flag Xs1 is set to "1" through the process of Step 1040 in FIG. 10, the CPU determines "YES" in Step 1505 and determines whether all of the conditions constituting the SOx detection conditions are satisfied in Step 1510.

When the SOx detection conditions are satisfied, the CPU determines "YES" in Step 1510 and performs the first SOx detection voltage control in Step 1515. Specifically, the CPU performs first application voltage control, second application voltage control, and third application voltage control which are described below as the first SOx detection voltage control.

First Application Voltage Control

A step-up sweep (1 second) of slowly stepping up the application voltage Vm from the first voltage V1 (0.4 V) to the second voltage V2 (0.8 V)

Second Application Voltage Control

Application voltage control (10 seconds) of maintaining the application voltage Vm at the same voltage as a voltage (0.8 V) at a time point at which the first application voltage control ends over a predetermined voltage maintaining time (a first time)

Third Application Voltage Control

A step-down sweep (1 second) of slowly stepping down the application voltage Vm from 0.8 V to the first voltage V1 (0.4 V)

When the first SOx detection voltage control is already performed at a time point at which the process of Step S1515 is performed, the CPU continues to perform the first SOx detection voltage control.

Thereafter, in Step 1520, the CPU determines whether the first SOx detection voltage control is completed.

When the first SOx detection voltage control is not completed, the CPU determines "NO" in Step 1520 and temporarily ends the routine in Step 1595.

When the first SOx detection voltage control is completed, the CPU determines "YES" in Step 1520 and acquires the first SOx detection parameter (the minimum current Ismn1) from the output current Im acquired by performing the first SOx detection voltage control in Step 1525. Thereafter, in Step 1527, the CPU applies the oxygen concentration detection application voltage Vaf (specifically, 0.4 V) across the first electrode 41a and the second electrode 41b for a predetermined time. Thereafter, in Step 1530, the CPU sets the value of the first SOx detection request flag Xs1 to "0" and sets the value of the second SOx detection request flag Xs2 to "1." Thereafter, the CPU temporarily ends this routine in Step 1595.

When the SOx detection conditions are not satisfied at a time point at which the process of Step 1510 is performed, the CPU determines "NO" in Step 1510 and applies the oxygen concentration detection application voltage Vaf (specifically, 0.4 V) across the first electrode 41a and the second electrode 41b in Step 1535. Thereafter, in Step 1540, the CPU sets the value of the first SOx detection request flag Xs1 to "0" and sets the value of the A/F detection request flag Xaf to "1." Thereafter, the CPU temporarily ends this routine in Step 1595.

Figure 16:
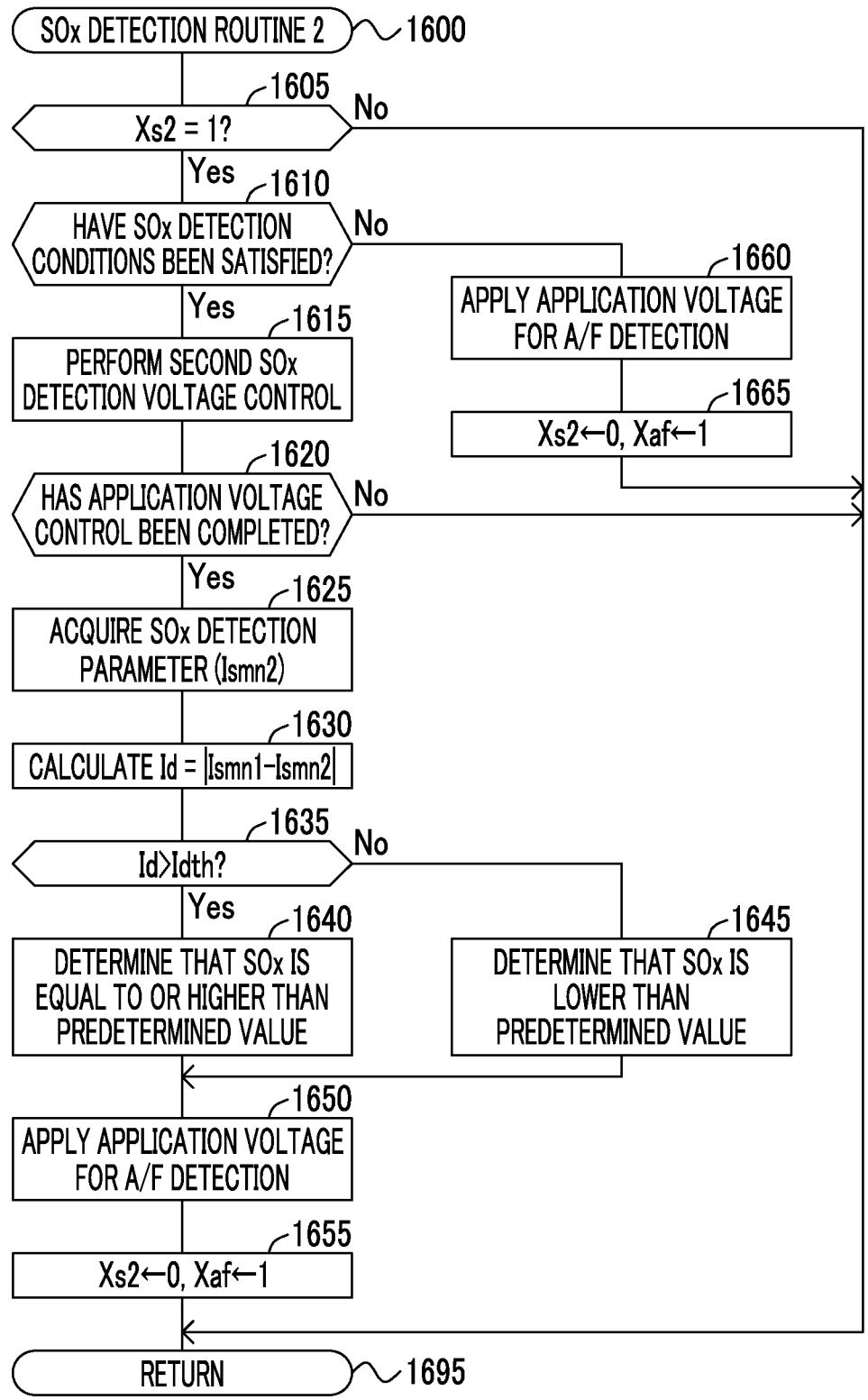
FIG. 16 is a flowchart illustrating SOx detection routine 2 which is performed by the CPU of the ECU in the gas detection device according to the third embodiment of the disclosure.

SOx detection routine 2 will be described below with reference to FIG. 16. At a predetermined time, the CPU starts this routine from Step 1600 of SOx detection routine 2 illustrated in FIG. 16 and determines whether the value of the second SOx detection request flag Xs2 is "1" in Step 1605.

SOx detection routine 2 functions substantially when acquisition of the first SOx detection parameter (the minimum current Ismn1) is completed (that is, when the second SOx detection request flag Xs2 is in the ON state (Xs2=1)). Accordingly, when the value of the second SOx detection request flag Xs2 is not "1" (that is, when the value of the second SOx detection request flag Xs2 is "0"), the CPU determines "NO" in Step 1605 and temporarily ends this routine in Step 1695.

Figure 15:
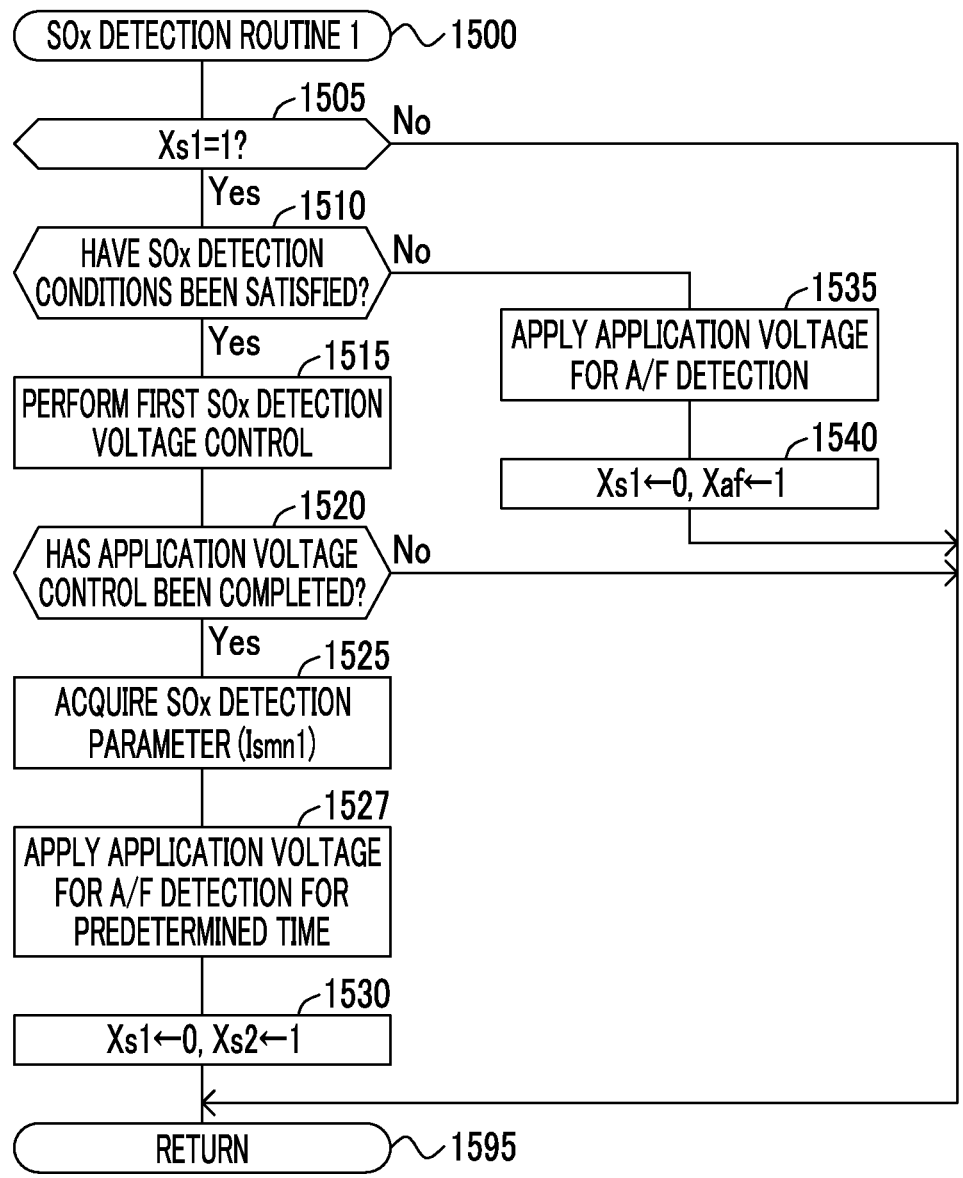
FIG. 15 is a flowchart illustrating SOx detection routine 1 which is performed by a CPU of an ECU in a gas detection device according to a third embodiment of the disclosure.

On the other hand, when the value of the second SOx detection request flag Xs2 is set to "1" through the process of Step 1530 in FIG. 15, the CPU determines "YES" in Step 1605 and determines whether all of the conditions constituting the SOx detection conditions are satisfied in Step 1610.

When the SOx detection conditions are satisfied, the CPU determines "YES" in Step 1610 and performs the second SOx detection voltage control in Step 1615. In the second SOx detection voltage control, the time of the second application voltage control is set to be longer than that in the first SOx detection voltage control such that the SOx decomposition period is longer than that of the first SOx detection voltage control. The second SOx detection voltage control is different from the first SOx detection voltage control, only in that the time of the second application voltage control is set to be longer, and the sweeping rates in the first application voltage control and the third application voltage control are the same as in the first SOx detection voltage control. Specifically, the CPU performs first application voltage control, second application voltage control, and third application voltage control which are described below as the second SOx detection voltage control.

First Application Voltage Control

A step-up sweep (1 second) of slowly stepping up the application voltage Vm from the first voltage V1 (0.4 V) to the second voltage V2 (0.8 V)

Second Application Voltage Control

Application voltage control (30 seconds) of maintaining the application voltage Vm at the same voltage as a voltage (0.8 V) at a time point at which the first application voltage control ends over a predetermined voltage maintaining time (a second time which is longer than the voltage maintaining time (the first time) of the first SOx detection voltage control)

Third Application Voltage Control

A step-down sweep (1 second) of slowly stepping down the application voltage Vm from 0.8 V to the first voltage V1 (0.4 V)

When the second SOx detection voltage control is already performed at a time point at which the process of Step S1615 is performed, the CPU continues to perform the second SOx detection voltage control.

Thereafter, in Step 1620, the CPU determines whether the second SOx detection voltage control is completed.

When the second SOx detection voltage control is not completed, the CPU determines "NO" in Step 1620 and temporarily ends this routine in Step 1695.

When the second SOx detection voltage control is completed, the CPU determines "YES" in Step 1620 and acquires the second SOx detection parameter (the minimum current Ismn2) from the output current Im acquired by performing the second SOx detection voltage control in Step S1625.

Thereafter, in Step 1630, the CPU calculates an absolute value of a difference (a difference magnitude Id) between the first SOx detection parameter (the minimum current Ismn1) acquired in the process of Step 1525 and the second SOx detection parameter (the minimum current Ismn2).

Thereafter, in Step 1635, the CPU determines whether the difference magnitude Id is greater than a threshold value (a threshold difference) Idth. The threshold difference Idth is a value suitable for determining whether the SOx concentration in the exhaust gas is equal to or higher than a predetermined value and is specified in advance by experiment or the like.

The CPU may change the value of the threshold difference Idth depending on the SOx decomposition period of the second SOx detection voltage control which is performed in Step 1615. Even when the SOx concentration in the exhaust gas is constant, a degree of decrease of the output current increases as the SOx decomposition period becomes longer and the threshold difference Idth may be changed in consideration of the increase in the degree of decrease of the output current Im. When the SOx concentration in the exhaust gas is constant, the difference magnitude Id also increases as the SOx decomposition period of the second SOx detection voltage control becomes longer. In some embodiments, the threshold difference Idth which is used to determine whether the SOx concentration is equal to or higher than a predetermined value is changed to increase as the SOx decomposition period of the second SOx detection voltage control which is performed in Step 1615 becomes longer. The CPU may determine the threshold difference Idth when the SOx decomposition period changes by applying the SOx decomposition period of the second SOx detection voltage control which is performed in Step 1615 to a predetermined lookup table.

When the difference magnitude Id is greater than the threshold difference Idth, the reoxidation current change is large and thus the CPU determines "YES" in Step 1635 and determines that the SOx concentration in the exhaust gas is equal to or higher than the predetermined value in Step 1640. Thereafter, the CPU performs Step 1650.

On the other hand, when the difference magnitude Id is equal to or less than the threshold difference Idth, the CPU determines "NO" in Step 1635 and determines that the SOx concentration in the exhaust gas is lower than the predetermined value in Step 1645. Thereafter, the CPU performs Step 1650.

In Step 1650, the CPU applies the oxygen concentration detection application voltage Vaf (specifically, 0.4 V) across the first electrode 41*a* and the second electrode 41*b*. Thereafter, in Step 1655, the CPU sets the value of the second SOx detection request flag Xs2 to "0" and sets the value of the A/F detection request flag Xaf to "1." Thereafter, the CPU temporarily ends this routine in Step 1695.

When the SOx detection conditions are not satisfied at a time point at which the process of Step 1610 is performed, the CPU determines "NO" in Step 1610 and applies the oxygen concentration detection application voltage Vaf (specifically, 0.4 V) across the first electrode 41*a* and the second electrode 41*b* in Step 1660. Thereafter, in Step 1665, the CPU sets the value of the second SOx detection request flag Xs2 to "0" and sets the value of the A/F detection request flag Xaf to 1." Thereafter, the CPU temporarily ends this routine in Step 1695.

As described above, the third detection device calculates the difference magnitude Id between the first SOx detection parameter which is acquired by performing the first SOx detection voltage control in which the SOx decomposition period is set to the first SOx decomposition period T1 and the second SOx detection parameter which is acquired by performing the second SOx detection voltage control in which the SOx decomposition period is set to the second SOx decomposition period T2 longer than the SOx decomposition period of the first SOx detection voltage control. Then, the third detection device determines whether the SOx concentration in the exhaust gas is equal to or higher than the predetermined value based on the difference magnitude Id.

The difference magnitude Id between the first SOx detection parameter and the second SOx detection parameter changes depending on the SOx concentration and serves as a parameter accurately indicating the SOx concentration, because an influence of an electrode state or the like (a current change based on capacitance and resistance of each electrode and capacitance and resistance of the solid electrolyte) of the gas sensor 30 is almost removed or reduced. The third detection device can accurately detect the SOx concentration based on the difference magnitude Id.

That is, since the output current Im when the first SOx detection voltage control is performed changes due to an influence of an electrode state or the like (capacitance and resistance of each electrode and capacitance and resistance of the solid electrolyte) of the gas sensor 30, the first SOx detection parameter includes a current change which is affected by the electrode state or the like of the gas sensor 30.

Since the output current Im when the second SOx detection voltage control is performed changes similarly due to an influence of an electrode state or the like (capacitance and resistance of each electrode and capacitance and resistance of the solid electrolyte), the second SOx detection parameter includes a current change which is affected by the electrode state or the like of the gas sensor 30 similarly to the first SOx detection parameter.

The electrode state or the like (capacitance and resistance of each electrode and capacitance and resistance of the solid electrolyte) of the gas sensor 30 changes due to aging or the like. The current change is a value varying depending on the electrode state or the like of the gas sensor 30. Accordingly, when the parameter used for the SOx concentration determination includes the current change, the value of the parameter changes in a case in which the SOx concentration in the exhaust gas is constant but the electrode state or the like of the gas sensor 30 varies. As a result, the likelihood that the first detection device can accurately detect the SOx concentration in the exhaust gas is lowered.

On the other hand, the current change is almost removed or reduced in the difference magnitude Id between the first SOx detection parameter and the second SOx detection parameter. Accordingly, the third detection device can accurately detect the SOx concentration based on the difference magnitude Id.

Fourth Embodiment

A gas detection device according to a fourth embodiment of the disclosure (hereinafter also referred to as a "fourth detection device") will be described below. The fourth detection device is different from the third detection device in only the following points. The third detection device calculates the difference magnitude Id between the first SOx detection parameter (the minimum current Ismn1) which is acquired from the output current Im when the first SOx detection voltage control is performed and the second SOx detection parameter (the minimum current Ismn2) which is acquired from the output current Im when the second SOx detection voltage control is performed. The third detection device determines whether the SOx concentration in the exhaust gas is equal to or higher than the first predetermined value based on the difference magnitude Id. On the other hand, the fourth detection device determines whether the SOx concentration in the exhaust gas is equal to or higher than a first predetermined value based on a magnitude of a difference Id. When it is determined that the SOx concentration in the exhaust gas is lower than the first predetermined value, the fourth detection device performs third SOx detection voltage control in which the SOx decomposition period is set to a third SOx decomposition period T3 which is longer than the second SOx decomposition period T2 of the second SOx detection voltage control. The fourth detection device calculates a magnitude of a difference Id' between the first SOx detection parameter (Ismn1) and a third SOx detection parameter (a minimum current Ismn3) which is acquired from the output current Im when the third SOx detection voltage control is performed. The fourth detection device determines whether the SOx concentration in the exhaust gas is equal to or higher than a second predetermined value set to be lower than the first predetermined value based on the calculated difference magnitude Id'. Hereinafter, this difference will be mainly described.

Specific Operation

A specific operation of the fourth detection device will be described below. The CPU of the ECU 20 performs the same sensor activation determination routine as the routine illustrated in FIG. 9, the same A/F detection routine as the routine illustrated in FIG. 10, the same SOx detection routine 1 as illustrated in FIG. 15, SOx detection routine 2 illustrated in FIG. 17, and Sox detection routine 3 illustrated in FIG. 18 at predetermined time intervals.

The sensor activation determination routine, the A/F detection routine, and SOx detection routine 1 are the same as the routines performed by the third detection device and have been described above. Accordingly, description thereof will not be repeated.

Figure 17:
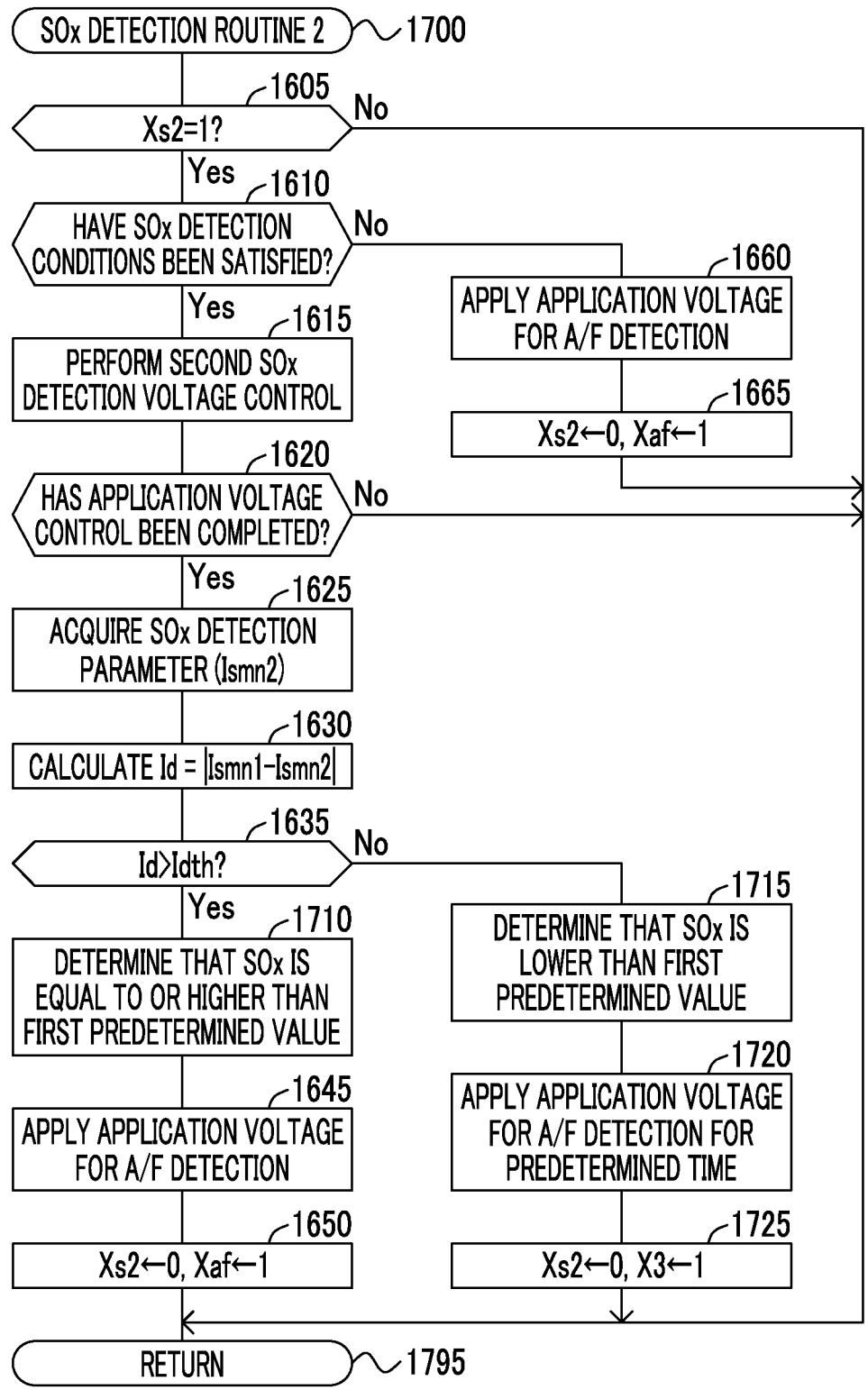
FIG. 17 is a flowchart illustrating SOx detection routine 2 which is performed by a CPU of an ECU in a gas detection device according to a fourth embodiment of the disclosure.

SOx detection routine 2 will be described below with reference to FIG. 17. SOx detection routine 2 illustrated in FIG. 17 is different from the SOx detection routine illustrated in FIG. 16 in only the following points. Steps 1640 and 1655 in FIG. 16 are replaced with Steps 1710 and 1715. Steps 1720 and 1725 are added between Steps 1645 and 1695 in FIG. 16. These differences will be mainly described below.

When the difference magnitude Id is greater than the threshold difference Idth, the reoxidation current change is large and thus the CPU determines "YES" in Step 1635 and determines that the SOx concentration in the exhaust gas is equal to or higher than the first predetermined value in Step 1710 (Step 1710). When the difference magnitude Id is equal to or less than the threshold difference Idth, the CPU determines "NO" in Step 1635 and determines that the SOx concentration in the exhaust gas is lower than the first predetermined value in Step 1715 (Step 1715). Thereafter, the CPU performs Step 1720. The oxygen concentration detection application voltage Vaf (specifically, 0.4 V) is applied across the first electrode 41a and the second electrode 41b for a predetermined time (Step 1720). Thereafter, the CPU performs Step 1725. The CPU sets the value of the second SOx detection request flag Xs2 to "0" and sets the value of a third SOx detection request flag Xs3 to "1" (Step 1725). Thereafter, the CPU temporarily ends this routine in Step 1795.

Figure 18:
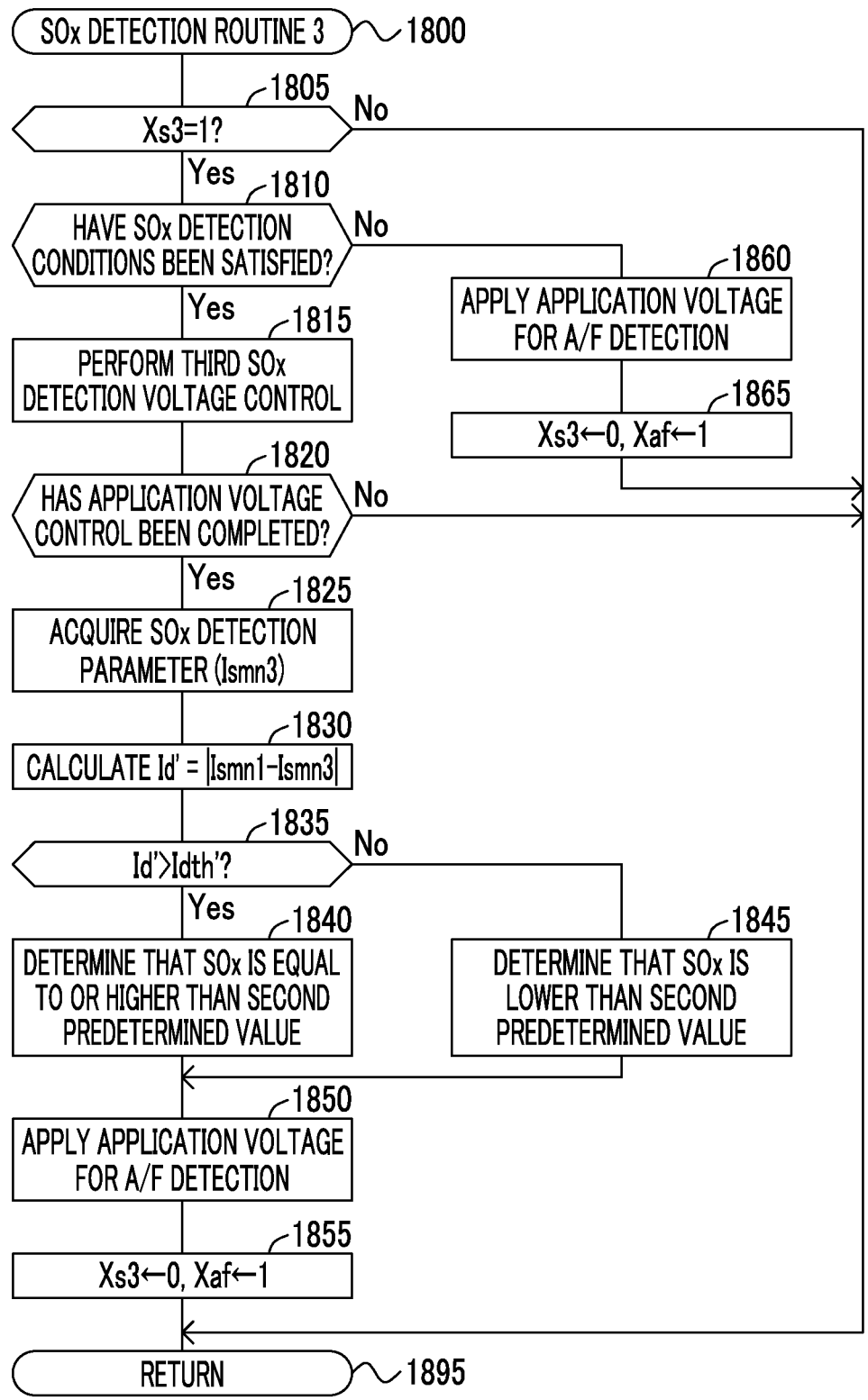
FIG. 18 is a flowchart illustrating SOx detection routine 3 which is performed by the CPU of the ECU in the gas detection device according to the fourth embodiment of the disclosure.

SOx detection routine 3 will be described below with reference to FIG. 18. At a predetermined time, the CPU starts this routine from Step 1800 of SOx detection routine 3 illustrated in FIG. 18 and determines whether the value of the third SOx detection request flag Xs3 is "1" in Step 1805.

SOx detection routine 3 functions substantially when it is determined in SOx detection routine 2 that the SOx concentration in the exhaust gas is lower than the first predetermined value. Accordingly, when the value of the third SOx detection request flag Xs3 is not "1" (that is, when the value of the third SOx detection request flag Xs3 is "0"), the CPU determines "YES" in Step 1805 and determines whether all of the conditions constituting the SOx detection conditions are satisfied in Step 1810.

When the SOx detection conditions are satisfied, the CPU determines "YES" in Step 1810 and performs the third SOx detection voltage control in Step 1815. In the third SOx detection voltage control, the time of the second application voltage control is set to be longer than that in the second SOx detection voltage control such that the SOx decomposition period is longer than that of the second SOx detection voltage control. The third SOx detection voltage control is different from the second SOx detection voltage control, only in that the time of the second application voltage control is set to be longer, and the sweeping rates in the first application voltage control and the third application voltage control are the same as in the second SOx detection voltage control. Specifically, the CPU performs first application voltage control, second application voltage control, and third application voltage control which are described below as the third SOx detection voltage control.

First Application Voltage Control

A step-up sweep (1 second) of slowly stepping up the application voltage Vm from the first voltage V1 (0.4 V) to the second voltage V2 (0.8 V)

Second Application Voltage Control

Application voltage control (60 seconds) of maintaining the application voltage Vm at the same voltage as a voltage (0.8 V) at a time point at which the first application voltage control ends over a predetermined voltage maintaining time (a third time which is longer than the voltage maintaining time (the second time) of the second SOx detection voltage control)

Third Application Voltage Control

A step-down sweep (1 second) of slowly stepping down the application voltage Vm from 0.8 V to the first voltage V1 (0.4 V)

When the third SOx detection voltage control is already performed at a time point at which the process of Step S1815 is performed, the CPU continues to perform the third SOx detection voltage control.

Thereafter, in Step 1820, the CPU determines whether the third SOx detection voltage control is completed.

When the third SOx detection voltage control is not completed, the CPU determines "NO" in Step 1820 and temporarily ends this routine in Step 1895.

When the third SOx detection voltage control is completed, the CPU determines "YES" in Step 1820 and acquires the third SOx detection parameter (the minimum current Ismn3) from the output current Im acquired by performing the third SOx detection voltage control in Step S1825.

Thereafter, in Step 1830, the CPU calculates an absolute value of a difference (a difference magnitude Id) between the first SOx detection parameter (the minimum current Ismn1) acquired in the process of Step 1525 and the third SOx detection parameter (the minimum current Ismn3).

Thereafter, in Step 1835, the CPU determines whether the difference magnitude Id' is greater than a threshold value (a threshold difference) Idth'. The threshold difference Idth' is a value suitable for determining whether the SOx concentration in the exhaust gas is equal to or higher than a second predetermined value set to be lower than the first predetermined value and is specified in advance by experiment or the like.

The CPU may change the value of the threshold difference Idth' depending on the SOx decomposition period of the third SOx detection voltage control which is performed in Step 1815. Even when the SOx concentration in the exhaust gas is constant, a degree of decrease of the output current increases as the SOx decomposition period becomes longer and the threshold difference Idth' may be changed in consideration of the increase in the degree of decrease of the output current Im. When the SOx concentration in the exhaust gas is constant, the difference magnitude Id' also increases as the SOx decomposition period of the third SOx detection voltage control becomes longer. In some embodiments, the threshold difference Idth' which is used to determine whether the SOx concentration is equal to or higher than the second predetermined value is changed to increase as the SOx decomposition period of the third SOx detection voltage control which is performed in Step 1815 becomes longer. The CPU may determine the threshold difference Idth' when the SOx decomposition period changes by applying the SOx decomposition period of the third SOx detection voltage control which is performed in Step 1815 to a predetermined lookup table.

When the difference magnitude Id' is greater than the threshold difference Idth', the reoxidation current change is large. Accordingly, the CPU determines "YES" in Step 1835 and determines whether the SOx concentration in the exhaust gas is equal to or higher than a second predetermined value in Step 1840. At this time, the CPU may store the purport indicating that the SOx concentration in the exhaust gas is equal to or higher than the second predetermined value in the backup RAM or may turn on a predetermined warning lamp. Thereafter, the CPU performs the process of Step 1850.

On the other hand, when the difference magnitude Id' is equal to or less than the threshold minimum current Idth', the CPU determines "NO" in Step 1835 and determines whether the SOx concentration in the exhaust gas is less than the second predetermined value in Step 1845. At this time, the CPU may store the purport indicating that the SOx concentration in the exhaust gas is less than the second predetermined value in the backup RAM or may turn off a predetermined warning lamp. Thereafter, the CPU performs the process of Step 1850.

In Step 1850, the CPU applies the oxygen concentration detection application voltage Vaf (specifically, 0.4 V) across the first electrode 41a and the second electrode 41b. Thereafter, in Step 1855, the CPU sets the value of the third SOx detection request flag Xs3 to "0" and sets the value of the A/F detection request flag Xaf to "1." Thereafter, the CPU temporarily ends this routine in Step 1895.

When the SOx detection conditions are not satisfied at a time point at which the process of Step 1810 is performed, the CPU determines "NO" in Step 1810 and applies the oxygen concentration detection application voltage Vaf (specifically, 0.4 V) across the first electrode 41a and the second electrode 41b in Step 1860. Thereafter, in Step 1865, the CPU sets the value of the third SOx detection request flag Xs3 to "0" and sets the value of the A/F detection request flag Xaf to 1." Thereafter, the CPU temporarily ends this routine in Step 1895.

As described above, the fourth detection device achieves the same advantages as the third detection device. When it is determined whether the SOx concentration in the exhaust gas is equal to or higher than a concentration (the second predetermined value) lower than that in the first SOx concentration determination, the fourth detection device sets the SOx decomposition period of the third SOx detection voltage control to be longer than that in the second SOx detection voltage control. Accordingly, even when the SOx concentration in the exhaust gas is low (the SOx concentration is lower than the first predetermined value), the difference depending on the SOx concentration (the difference between when the SOx concentration is equal to or higher than a second predetermined value and when the SOx concentration is lower than the second predetermined value) appears distinctly in the different magnitude Id'. Accordingly, it is possible to accurately determine whether the SOx concentration in the exhaust gas is equal to or higher than the second predetermined value (determine whether the SOx concentration in the exhaust gas is equal to or lower than the SOx concentration lower than that in the first SOx concentration determination).

Modified Examples

While embodiments of the disclosure have been described above, the disclosure is not limited to the embodiments and can employ various modified examples based on the technical concept of the disclosure.

In the above-mentioned embodiments, the SOx detection parameter is not limited to the "minimum value Ismn of the output current Im in a period in which the application voltage Vm is in the detection voltage range during the step-down sweep," but a value having a correlation with the output current Im in the period in which the application voltage Vm is in the detection voltage range during the step-down sweep may be acquired as the SOx detection parameter.

Figure 19:
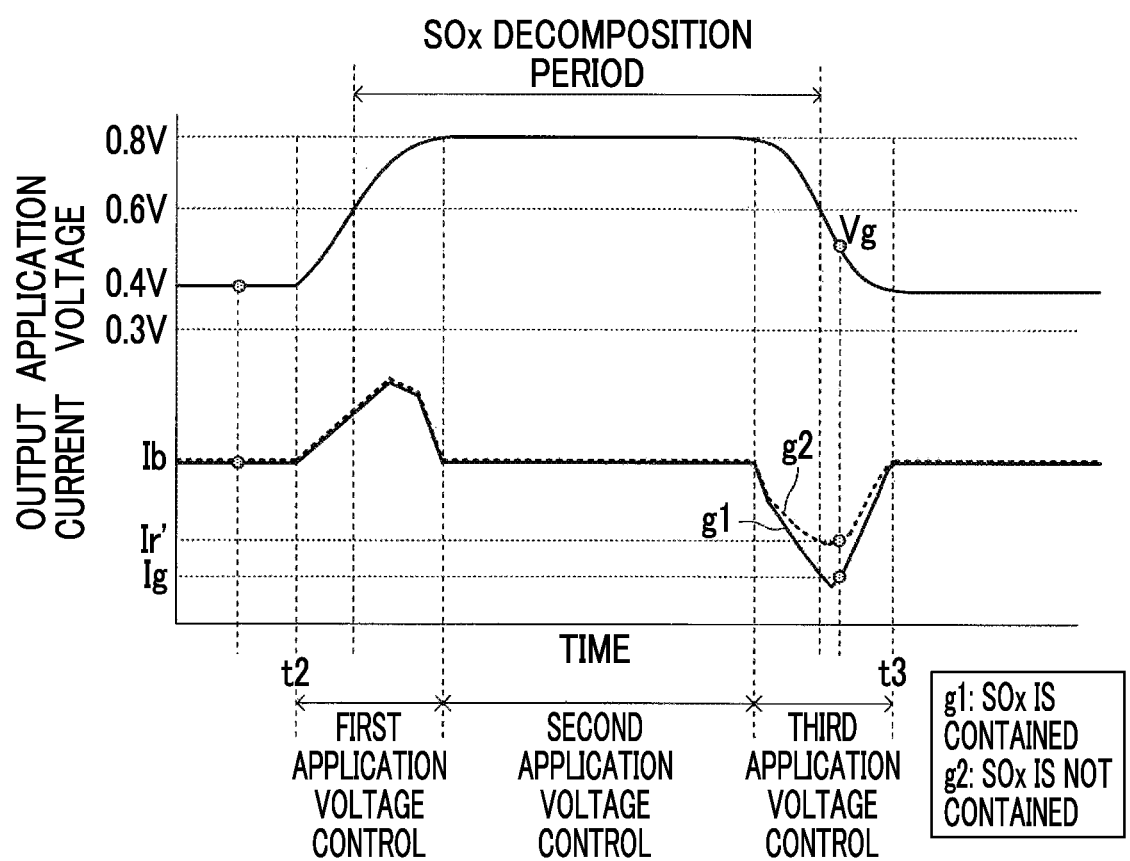
FIG. 19 is a graph illustrating a relationship between an application voltage and an output current.

For example, in the embodiments, as illustrated in FIG. 19, the output current Im when the application voltage Vm is a current acquisition voltage Vg during the step-down sweep (during the third application voltage control) may be acquired as the SOx detection parameter. In this case, the current acquisition voltage Vg is selected in a range (a detection voltage range) which is equal to or higher than a fourth voltage higher than the lower limit voltage (the first voltage V1) of the step-down sweep and equal to or higher than the third voltage Vsem equal to or lower than the SOx decomposition start voltage (0.6 V).

In the embodiments, as illustrated in FIG. 19, the output current Im before the SOx detection voltage control is performed may be acquired as a second current Ib and an absolute value of a difference (a difference magnitude) between the second current Ib and the SOx detection parameter may be acquired as the SOx detection parameter which is used for detection of the SOx concentration.

The SOx detection parameter (Ismn) changes depending on the SOx concentration in the exhaust gas. Since the output current Im changes due to an influence of an oxygen concentration in the exhaust gas, the SOx detection parameter also changes due to the influence of the oxygen concentration in the exhaust gas, but the degree of influence appears in the output current Im (the second current Ib) when the application voltage Vm is a A/F detection voltage Vaf immediately before the SOx detection voltage control is performed. Accordingly, the difference magnitude between the second current Ib and the SOx detection parameter serves as a parameter accurately indicting a concentration of sulfur oxides with not being affected (reducing) the oxygen concentration in the exhaust gas (the air-fuel ratio A/F of the engine).

The output current Im which can be used as the second current Ib is not limited to the "output current Im when the application voltage Vm is the A/F detection voltage Vaf," but another output current Im other than that may be used as the second current Ib. That is, an output current Im when the application voltage Vm is the same voltage as a voltage at which the output current Im when the SOx is contained in the exhaust gas and the output current Im when SOx is not contained in the exhaust gas have the same magnitude, that is, an output current Im when the oxygen concentration in the exhaust gas can be considered to be the same as the "oxygen concentration in the exhaust gas when the SOx detection parameter is acquired" and a decomposition current of oxygen with the concentration is included in the second current Ib, may be used as the second current Ib.

In the embodiments, it is determined whether the SOx concentration in the exhaust gas is equal to or higher than the predetermined value by comparing the SOx detection parameter (Ismn) or the difference magnitude (Id, Id') of the SOx detection parameter with a threshold value. On the other hand, in the embodiments, the SOx concentration in the exhaust gas may be detected (acquired) based on the SOx detection parameter or the difference magnitude of the SOx detection parameter. For example, the ECU 20 may detect the SOx concentration by applying the SOx detection parameter (or the difference magnitude thereof) to a "map indicating a relationship between the SOx detection parameter (or the difference magnitude thereof) and the SOx concentration" stored in the ROM. In this case, the ECU 20 detects the SOx concentration depending on the SOx detection parameter (or the difference magnitude thereof).

In the second embodiment, after it is determined that the SOx concentration in the exhaust gas is lower than the second predetermined value, the following process may be performed once or more. That is, when it is determined in the previous SOx concentration determination that the SOx concentration in the exhaust gas is lower than the predetermined value, SOx detection voltage control in which the SOx decomposition period is set to be longer than the SOx decomposition period of the previous SOx detection voltage control may be additionally performed and the SOx detection parameter may be acquired from the output current at that time. Then, based on the acquired SOx detection parameter, it is determined whether the SOx concentration in the exhaust gas is equal to or higher than a predetermined value which is set to a concentration lower than the predetermined value in the previous control.

In the fourth embodiment, after it is determined that the SOx concentration in the exhaust gas is lower than the second predetermined value, the following process may be performed once or more. That is, when it is determined in the previous SOx concentration determination that the SOx concentration in the exhaust gas is lower than the predetermined value, SOx detection voltage control in which the SOx decomposition period is set to be longer than the SOx decomposition period of the previous SOx detection voltage control is additionally performed and the SOx detection parameter is acquired from the output current at that time. A magnitude of a difference between the first SOx detection parameter and the acquired SOx detection parameter is calculated. Then, based on the calculated magnitude of the difference, it is determined whether the SOx concentration in the exhaust gas is equal to or higher than a predetermined value which is set to a concentration lower than the predetermined value in the previous control.

What is claimed is:

1. A gas detection device comprising:
an element portion which is disposed in an exhaust gas passage of an internal combustion engine, which includes an electrochemical cell including a solid electrolyte with oxide ion conductivity and a first electrode and a second electrode which are formed on surfaces of the solid electrolyte, and a diffusion resistor formed of a porous material being able to transmit an exhaust gas flowing in the exhaust gas passage, and in which the exhaust gas flowing in the exhaust gas passage reaches the first electrode via the diffusion resistor;
a power supply circuit configured to apply a voltage across the first electrode and the second electrode;
a current detection sensor configured to detect an output current which is a current flowing between the first electrode and the second electrode; and
an electronic control unit configured to control an application voltage which is a voltage applied across the first electrode and the second electrode using the power supply circuit, to acquire the output current using the current detection sensor, and to perform determination of whether sulfur oxides with a predetermined concentration or more is contained in the exhaust gas or detection of a concentration of sulfur oxides in the exhaust gas based on the acquired output current, wherein the electronic control unit performs detection voltage control including first application voltage control, second application voltage control, and third application voltage control using the power supply circuit, the first application voltage control is application voltage control of performing a step-up sweep of stepping up the application voltage from a first voltage, which is selected from a first voltage range which is higher than a lower limit voltage of a limiting current region in which the output current is a limiting current of oxygen and lower than a decomposition start voltage of sulfur oxides, to a second voltage which is higher than the decomposition start voltage of sulfur oxides, the second application voltage control is application voltage control of maintaining the application voltage to be equal to or higher than the decomposition start voltage of sulfur oxides over a predetermined voltage maintaining time from a time point at which the first application voltage control ends after the first application voltage control, the third application voltage control is application voltage control of performing a step-down sweep of stepping down the application voltage from a voltage at a time point at which the second application voltage control ends to the first voltage at a predetermined step-down rate after the second application voltage control, the electronic control unit acquires a parameter, which has a correlation with a degree of a reoxidation current change of the output current, which appears in a voltage range below the decomposition start voltage of sulfur oxides, due to a current flowing between the first electrode and the second electrode due to return of sulfurs adsorbed on the first electrode to sulfur oxides by a reoxidation reaction in the first electrode when the application voltage is less than the decomposition start voltage of sulfur oxides during the step-down sweep, the degree of change of the output current increasing as the concentration of sulfur oxides in the exhaust gas increases, based on the output current, and performs determination of whether the concentration of sulfur oxides in the exhaust gas is equal to or higher than a predetermined value or detection of the concentration of sulfur oxides in the exhaust gas based on the acquired parameter, and the predetermined step-down rate in the step-down sweep is set to a rate at which a current change indicating the reoxidation current change appears.

2. The gas detection device according to claim 1, wherein the second application voltage control is application voltage control of maintaining the application voltage at the second voltage over the voltage maintaining time.

3. The gas detection device according to claim 1, wherein the electronic control unit sets the predetermined step-down rate to a rate at which the rate of the reoxidation reaction increases from a time point at which the application voltage becomes a voltage in a voltage range which is included in the first voltage range and is higher than the first voltage.

4. The gas detection device according to claim 1, wherein when it is determined that sulfur oxides with the predetermined concentration or more is not contained in the exhaust gas, the electronic control unit performs the first application voltage control, corrected second application voltage control of maintaining the application voltage at a voltage equal to or higher than the decomposition start voltage of sulfur oxides over a voltage maintaining time which is longer than the voltage maintaining time in the detection voltage control which is performed for the determination, and the third application voltage control, acquires the parameter again during the step-down sweep in the third application voltage control subsequent to the corrected second application voltage control, and performs determination of whether the concentration of sulfur oxides in the exhaust gas is equal to or higher than a second predetermined value lower than the predetermined value again based on the acquired parameter.

5. The gas detection device according to claim 1, wherein the electronic control unit performs the detection voltage control including the second application voltage control in which the voltage maintaining time is set to a first time to acquire the parameter as a first parameter, then performs the detection voltage control including the second application voltage control in which the voltage maintaining time is set to a second time longer than the first time to acquire the parameter as a second parameter, calculates a magnitude of a difference between the acquired first parameter and the acquired second parameter, and performs determination of whether the concentration of sulfur oxides in the exhaust gas is equal to or higher than a predetermined value or detection of the concentration of sulfur oxides in the exhaust gas based on the calculated magnitude of the difference.

6. The gas detection device according to claim 5, wherein when it is determined that sulfur oxides with the predetermined concentration or higher is not contained in the exhaust gas in the determination using the magnitude of the difference between the first parameter and the second parameter, the electronic control unit performs the detection voltage control including the second application voltage control in which the voltage maintaining time is set to a third time longer than the second time to acquire the parameter as a third parameter, calculates a magnitude of a difference between the acquired first parameter and the acquired third parameter, and performs determination of whether the concentration of sulfur oxides in the exhaust gas is equal to or higher than a predetermined value lower than the predetermined value again based on the calculated magnitude of the difference.

7. The gas detection device according to claim 1, wherein the current detection sensor is an ammeter.

* * * * *

UNITED STATES PATENT AND TRADEMARK OFFICE
CERTIFICATE OF CORRECTION

PATENT NO. : 10,690,629 B2
APPLICATION NO. : 15/841941
DATED : June 23, 2020
INVENTOR(S) : Kazuhisa Matsuda, Kazuhiro Wakao and Keiichiro Aoki It is certified that error appears in the above-identified patent and that said Letters Patent is hereby corrected as shown below:

On the Title Page

Item (72), inventor 1, city, delete "Susono" and insert --Susono-shi Shizuoka-ken--, therefor.

Item (72), inventor 2, city, delete "Susono" and insert --Susono-shi Shizuoka-ken--, therefor.

Item (72), inventor 3, city, delete "Shizuoka-ken" and insert --Sunto-gun Shizuoka-ken--, therefor.

Signed and Sealed this
First Day of September, 2020

Andrei Iancu
*Director of the United States Patent and Trademark Office*